(12) United States Patent
Brown et al.

(10) Patent No.: US 7,371,744 B2
(45) Date of Patent: May 13, 2008

(54) BIOLOGICALLY ACTIVE METHYLENE BLUE DERIVATIVES

(75) Inventors: Stanley B. Brown, Burley-in-Wharfedale (GB); Cassandra C. O'Grady, Leeds (GB); John Griffiths, Leeds (GB); Kirste J. Mellish, Morley (GB); David I. Vernon, Chapel Allerton (GB)

(73) Assignee: Photopharmica Limited, Leeds (GB)

( * ) Notice: Subject to any disclaimer, the term of this patent is extended or adjusted under 35 U.S.C. 154(b) by 425 days.

(21) Appl. No.: 10/723,420

(22) Filed: Nov. 26, 2003

(65) Prior Publication Data
US 2004/0147508 A1 Jul. 29, 2004

Related U.S. Application Data

(63) Continuation-in-part of application No. PCT/GB02/02278, filed on May 30, 2002.

(30) Foreign Application Priority Data

May 30, 2001 (GB) ................... 0113121.8
Oct. 5, 2001 (GB) ................... 0123945.8

(51) Int. Cl.
*A61K 31/54* (2006.01)
(52) U.S. Cl. .................. 514/224.8
(58) Field of Classification Search ............. 514/224.8
See application file for complete search history.

(56) References Cited

U.S. PATENT DOCUMENTS

| | | | |
|---|---|---|---|
| 4,622,395 | A | 11/1986 | Bellus et al. |
| 4,880,769 | A | 11/1989 | Dix et al. |
| 5,085,947 | A | 2/1992 | Saito et al. |
| 5,085,974 | A | 2/1992 | Frass et al. |
| 5,239,405 | A | 8/1993 | Varaprasad et al. |
| 5,344,928 | A | 9/1994 | Masuya et al. |
| 5,358,876 | A | 10/1994 | Inoue et al. |
| 5,532,171 | A | 7/1996 | Motsenbocker |
| 5,545,516 | A | 8/1996 | Wagner |
| 5,611,793 | A * | 3/1997 | Wilson et al. |
| 5,685,994 | A | 11/1997 | Johnson |
| 5,882,627 | A | 3/1999 | Pomerantz |
| 6,183,764 | B1 * | 2/2001 | Shanbrom |
| 6,251,127 | B1 | 6/2001 | Biel |
| 6,551,346 | B2 | 4/2003 | Crossley |
| 6,562,295 | B1 | 5/2003 | Neuberger |
| 6,623,513 | B2 | 9/2003 | Biel |
| 6,952,392 | B2 | 10/2005 | Vig et al. |
| 7,101,977 | B2 | 9/2006 | Rosenblum et al. |
| 7,176,308 | B2 | 2/2007 | Vig et al. |
| 7,220,879 | B2 | 5/2007 | Bass et al. |
| 7,229,447 | B1 | 6/2007 | Biel |
| 2002/0061330 | A1 * | 5/2002 | Chowdhary et al. ....... 424/450 |
| 2002/0183808 | A1 | 12/2002 | Biel |
| 2003/0158204 | A1 | 8/2003 | Galey |
| 2004/0055965 | A1 | 3/2004 | Hubig et al. |
| 2004/0147508 | A1 | 7/2004 | Brown et al. |
| 2004/0213736 | A1 | 10/2004 | Wischik et al. |
| 2007/0161625 | A1 | 7/2007 | Brown et al. |

FOREIGN PATENT DOCUMENTS

| | | |
|---|---|---|
| DE | 19640758 C2 | 11/1999 |
| EP | 0128414 | 12/1984 |
| GB | 2373787 | 2/2002 |
| JP | 63187154 | 8/1988 |
| JP | 2001124699 | 5/2001 |
| WO | WO 91/16911 * | 11/1991 |
| WO | WO 96/30766 | 10/1996 |
| WO | WO 99/25314 | 5/1999 |
| WO | WO 01/62289 * | 8/2001 |
| WO | WO 01/70699 | 9/2001 |
| WO | WO 02/096896 | 12/2002 |

OTHER PUBLICATIONS

"Methylene Blue" (Monograph No. 5979). The Merck Index (Eleventh Edition). Merck & Co., Inc. 1989. p. 954.*
Wainwright et al. "Photobactericidal Activity of Phenothiazinium Dyes Against Methicillin-Resistant Strans of *Staphylococcus aureus*". FEMS Microbiology Letters, 160 (1998). pp. 177-181.*

(Continued)

Primary Examiner—Ardin H. Marschel
Assistant Examiner—Leslie A Royds
(74) Attorney, Agent, or Firm—Nixon & Vanderhye P.C.

(57) ABSTRACT

A phenothiazinium compound of Formula (I):

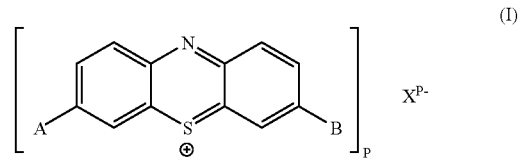

wherein:
A and B each independently is

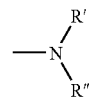

in which R' and R" each independently is a linear, branched or cyclic hydrocarbon group, or R' and R" together with the N atom to which they are attached form an optionally substituted 5-, 6- or 7-membered ring;
and where $X^{P-}$ is a counteranion and P is 1, 2 or 3;
except for the compounds in which A and B are both either
—$N(CH_3)_2$ or
—$N(CH_2CH_3)_2$ for use in a treatment that requires removal, deactivation or killing of unwanted tissues or cells.

13 Claims, 17 Drawing Sheets

OTHER PUBLICATIONS

Mutschler et al. Drug Actions: Basic Principles and Therapeutic Aspects. Medpharm Scientific Publishers, 1995. pp. 515-580.*

Merriam-Webster Dictionary [Online]. "Remove". [Retrieved Mar. 16, 2007]. Retrieved from the Internet: <URL: http://www.m-w.com/dictionary/remove>.*

Poster titled "*In Vitro Photodynamic Activity of a Series of novel Methylene Blue Analogues*" by Mellish et al., Centre for Photobiology and Photodynamic Therapy, Jul. 2000, 1 page.

www.sigma-aldrich.com, M9140 Methylene Blue, 2006.

www.sigma-aldrich.com, T3260 Toluidine Blue O, 2006.

www.sigma-aldrich.com, T7029 Thionin acetate, 2006.

www.sigma-aldrich.com, A6270 Azure A chloride, 2006.

www.sigma-aldrich.com, A4043 Azure B, 2006.

www.sigma-aldrich.com, 11667 Azure C, 2006.

www.sigma-aldrich.com, 302643 Trypan Blue, 2006.

www.sigma-aldrich.com, 211109 Methylene Green zinc chloride double salt, 2006.

www.sigma-aldrich.com, N3013 Nile Red, 2006.

Valduga et al, "Effect of extracellularly generated singlet oxygen on Gram-positive and Gram-negative bacteria", J. Photochem. Photobiol. B: Biol. 21:81-86 (1993).

Weng et al, "Adsorption of cationic dye (methylene blue) onto spent activated clay", Journal of Hazardous Materials 144:355-362 (2007).

Gürses et al, "The adsorption kinetics of the cationic dye, methylene blue, onto clay", Journal of Hazardous Materials B131:217-228 (2006).

Methylene blue clay test kit, Website accessed Aug. 9, 2007, http://www.ofite.com/products/Drilling/Kits/168-00.htm.

Fujii et al, "Synthesis of 2-(D-*Arabino*-terta-hydroxybutyl)pyrazine-5-sulfonic Acid", Agric. Biol. Chem. 46(8):2169-2172 (1982).

Wainwright et al, "Increased cytotoxicity and phototoxicity in the methylene blue series via chromophore methylation", Journal of Photochemistry and Photobiology B: Biology 40:233-239 (1997).

Wainwright, "Photodynamic therapy—from dyestuffs to high-tech clinical practice", Rev. Prog. Color. 34:95-109 (2004).

Wainwright, "Photodynamic antimicrobial chemotherapy (PACT)", Journal of Antimicrobial Chemotherapy 42:13-28 (1998).

Kiernan, Dyes and other colorants in microtechnique and biomedical research Color. Technol. 122:1-21 (2006).

Wainwright, "Non-porphyrin Photosensitizers in Biomedicine", Chemical Society Reviews, pp. 351-359 (1996).

Colour Index, Third Edition, vol. 4 (1971), (The Society of Dyers and Colourists/American Association of Textile Chemists and Colorists), http://www.colour-index.org.

The Sigma-Aldrich Handbook of Stains, Dyes and Indicators, Floyd J. Green (Aldrich Chemical Company Inc., Milwaukee, Wisconsin (1990).

Stains and Dyes—Certified and Non-Certified, http://www.sigmaaldrich.com [http://www.sigmaaldrich.com/Area_of_Interest/Research_Essentials/Hematology_and_Histology/Product_Lines/Stains_and_Dyes.html.].

Bernthsen, "Studien in der Methylenblaugruppe", Justus Liebig's Annalen Der Chemie 251, Abschnitt 6, Homologe Indamine und Thioninfarbstoffe, pp. 83-97 (1888) and English Translation.

Moura et al, "Synthetic routes to 3,7-*bis*(dialkylamino)phenothiazin-5-ium compounds", Current Drug Targets 4(2):133-142 (2003).

http://photopharmica.com/news/01_07_07.htm, 2007 "photopharmica announces successful phase II data".

Mellish et al, "In Vitro Photodynamic Activity of a Series of Methylene Blue Analogues". Photochemistry and Photobiology 75(4):392-397 (2002).

* cited by examiner

Figure 1

Symmetrical phenothiazinium salts: *in vivo* activity at 1h

Figure shows % cross sectional tumour necrosis at 72h post-PDT. All drugs were administered i.v. at a dose of 16.7μmol/kg. At 1h post drug administration light (60J/cm$^2$, 50mW/cm$^2$) was administered superficially.

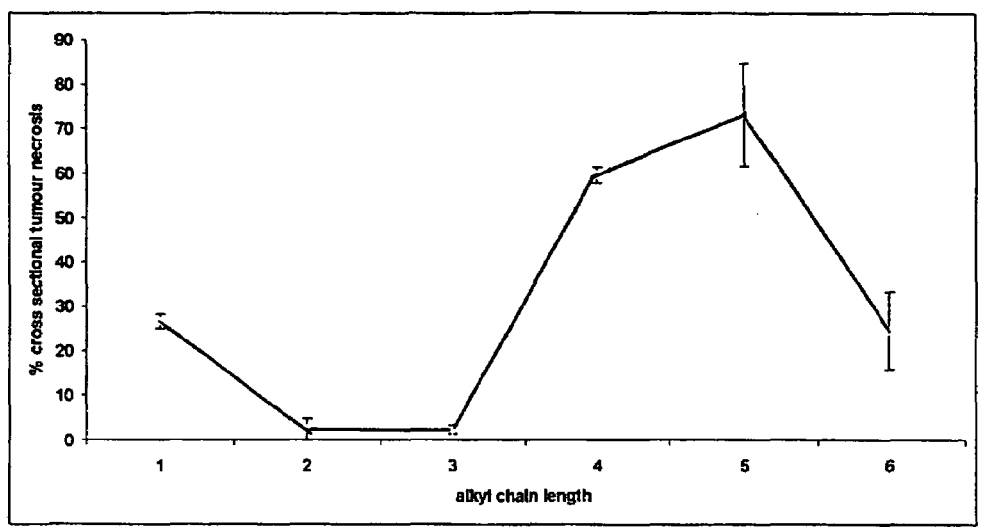

| Symmetrical phenothiazinium salt | Alkyl chain length | Vehicle | Wavelenght (nm ± 15) | %area | s.e.m |
|---|---|---|---|---|---|
| Methyl | 1 | Phys. saline | 685 | 26.70 | 1.60 |
| Ethyl | 2 | Phys. saline | 630 | 2.38 | 2.38 |
| Propyl | 3 | 2%DMSO/H2O | 630 | 2.27 | 0.99 |
| Butyl | 4 | 2%DMSO/H2O | 660 | 59.74 | 1.78 |
| Pentyl | 5 | 2%DMSO/H2O | 685 | 73.31 | 11.57 |
| Hexyl | 6 | 2%DMSO/H2O | 660 | 24.71 | 8.74 |

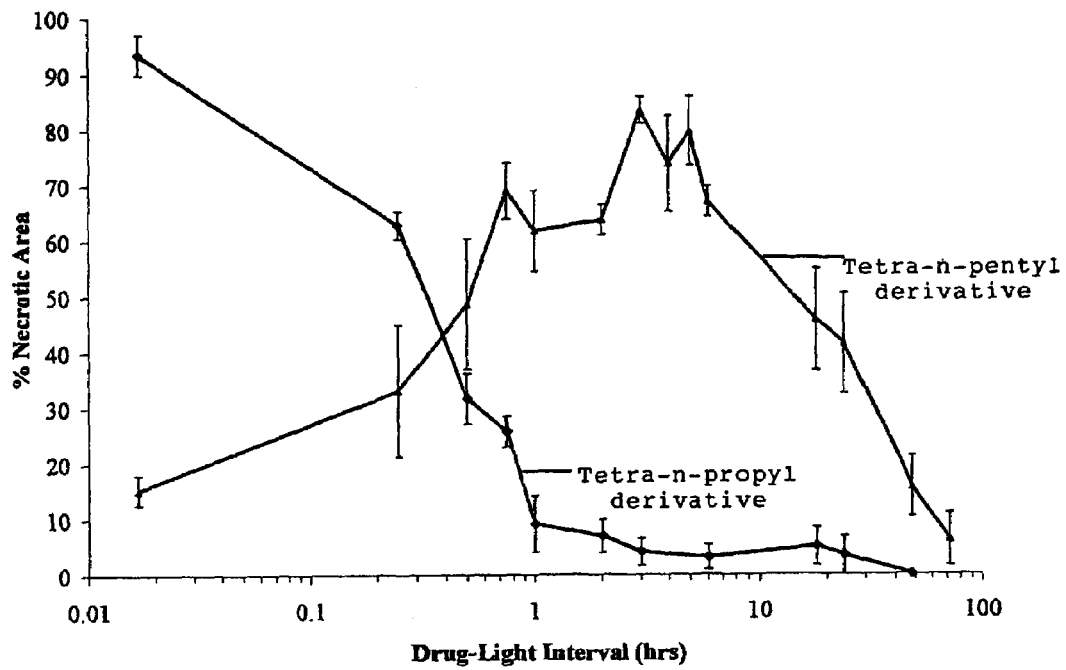
Figure 2: Area of tumour necrosis (expressed as a % total section area) 72 hrs after PDT with tetra-n-propyl and tetra-n-pentyl derivative (16.7µmolkg$^{-1}$, 660nm light @ 50mWcm$^{-2}$, 60Jcm$^{-2}$). Data points represent mean + SEM (n=6, each reading measured in triplicate).

Figure 3

Skin photosensitivity- murine ear swelling response

CBA/Gy mice were injected with sensitiser at 16.7 µmol/kg. At 24h post drug injection ears were exposed to broad band white light from a xenon arc lamp ($25J/cm^2$, $30mW/cm^2$). % Change in ear thickness was measured as :

(ear thickness at 24h post illumination - ear thickness pre-illumination) / ear thickness pre-illumination x 100

Increased % change in ear thickness measures increased skin photosensitivity.

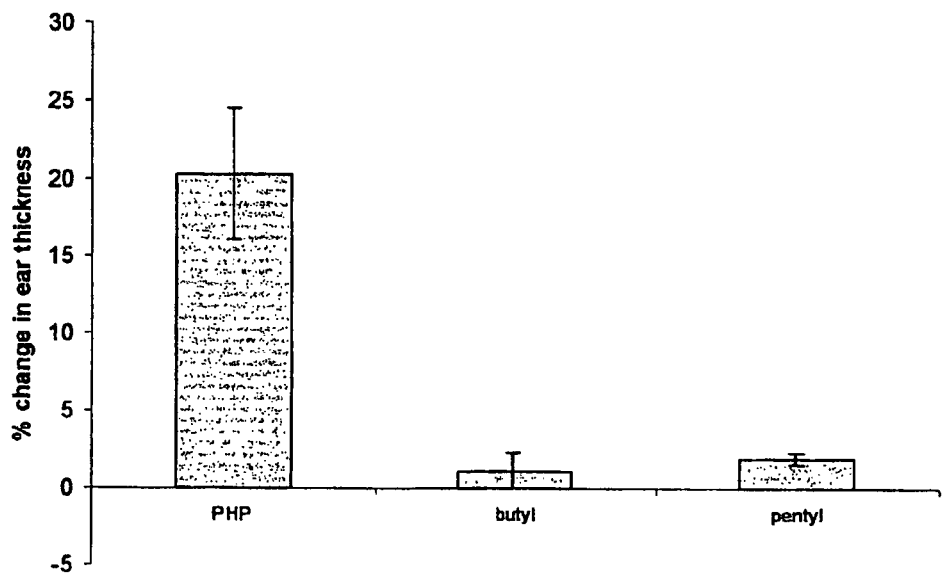

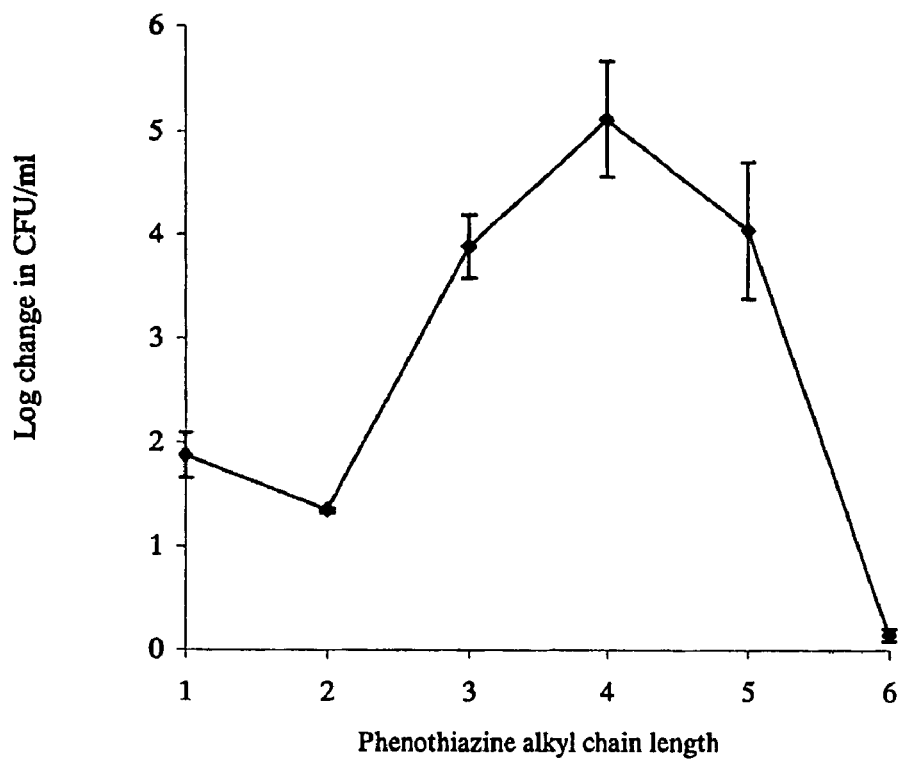
Figure 4 Log change in CFU/ml of *E.coli* incubated for 30 minutes with 10µM phenothiazine and illuminated for 60 minutes at 1.3mW/cm$^{-2}$

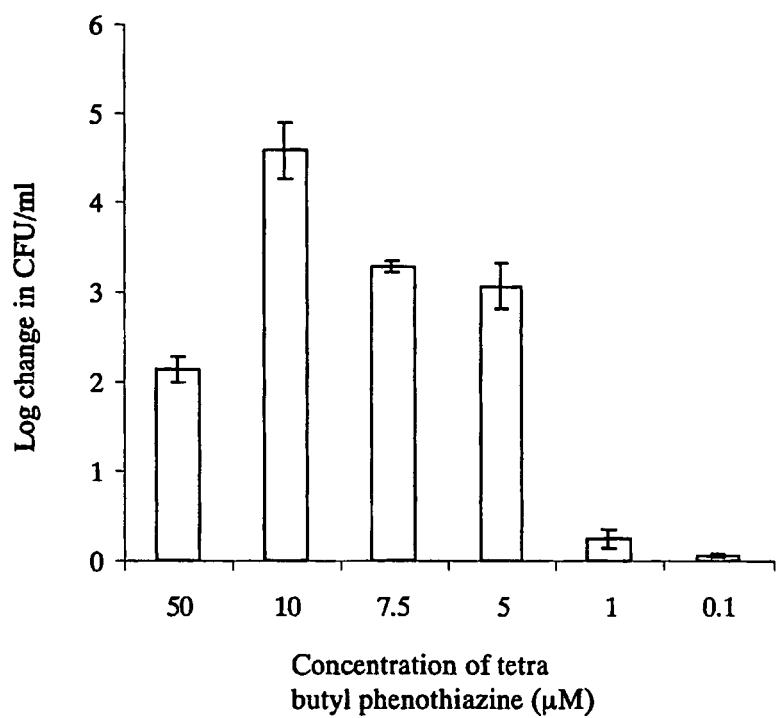
Figure 5 Log change in CFU/ml of *E.coli* incubated for 30 minutes with different concentrations of tetra butyl phenothiazine and illuminated for 15 minutes at 1.3mW/cm$^{-2}$

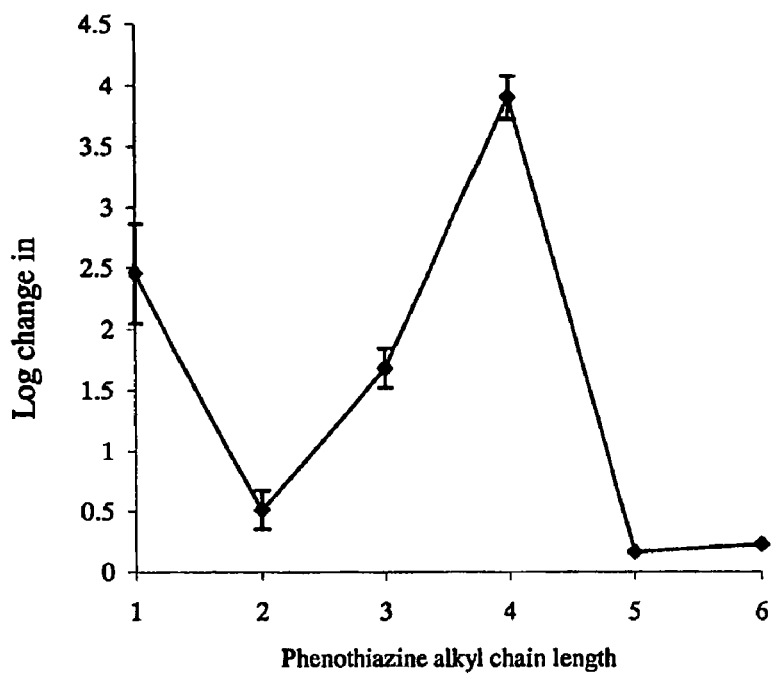
Figure 6 Log change in CFU/ml of *E.coli* in the stationary phase of growth following incubation for 30 minutes with 10μM phenothiazine and illuminated for 60 minutes at 1.3mWcm$^{-2}$

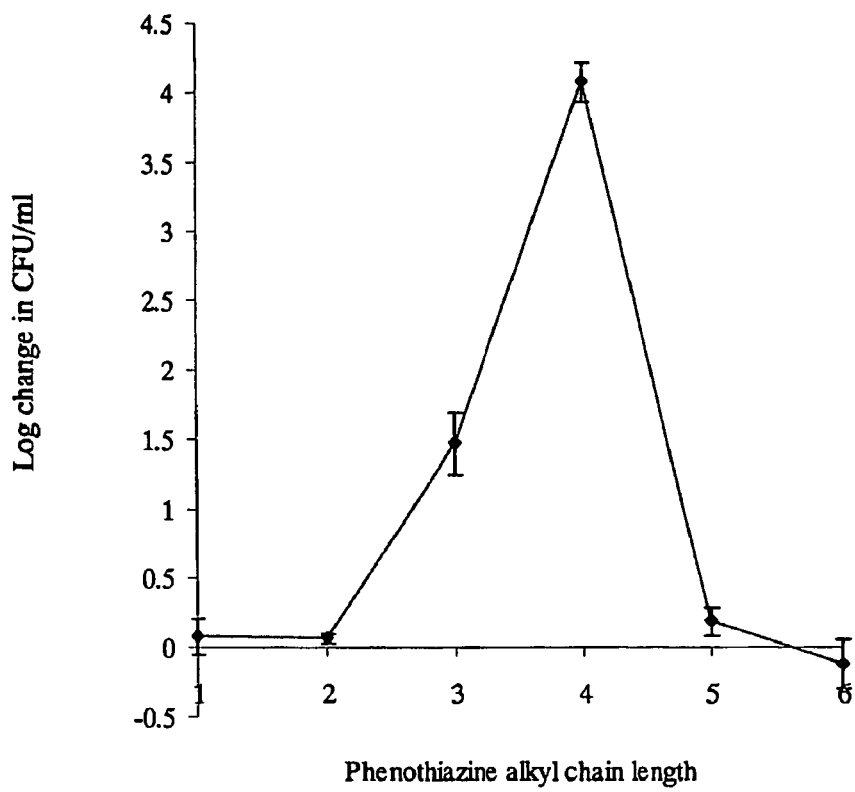
Figure 7 Log change in CFU/ml of *E.coli* resuspended in nutrient media. Cell were incubated for 30 minutes with 10μM phenothiazine and illuminated for 60 minutes at 1.3mW/cm$^{-2}$

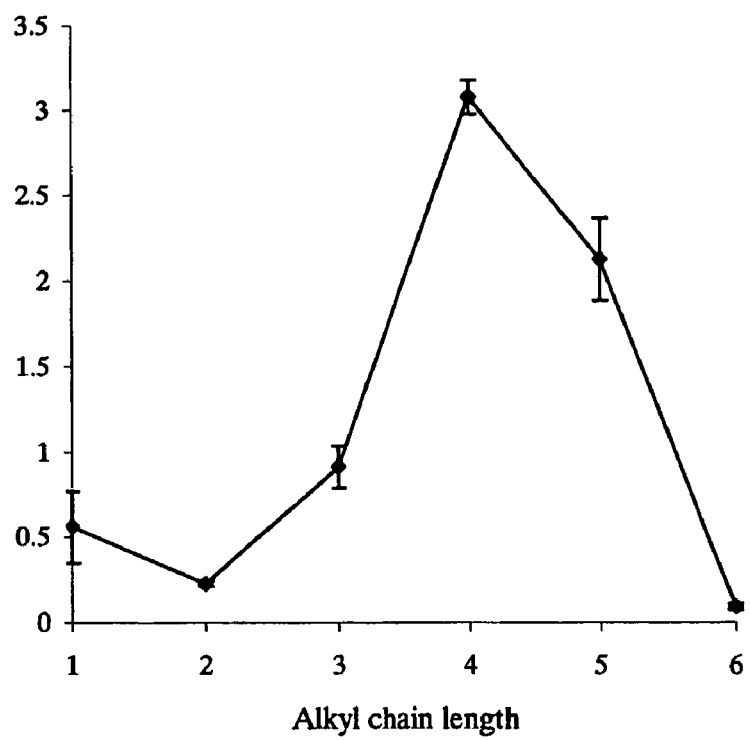
Figure 8 Log change in CFU/ml of *E.coli* following incubation with 10μM phenothiazine for 30 minutes. Illumination was with laser light (664nm) for 4 minutes at 0.1W

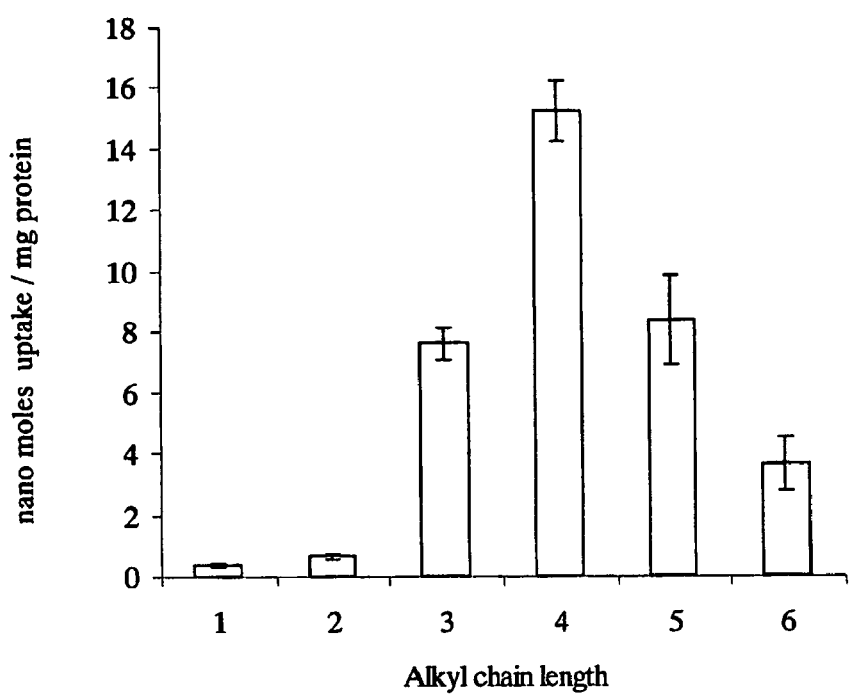
Figure 9 Uptake of 10µM phenothiazine into *E.coli* cells following a 30 minute incubation. Cells were washed twice in 0.1M pH7.0 potassium phosphate buffer to remove extra-cellular or loosely bound sensitiser.

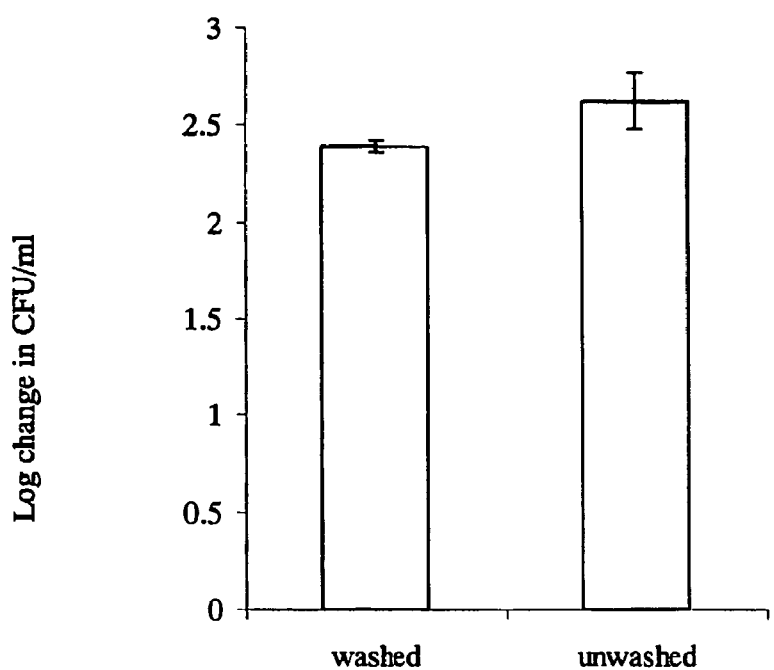
Figure 10 Log change in CFU/ml of *E.coli* cells incubated with 10μM tetra butyl phenothiazine. Cells were washed twice with 0.1M pH7 potassium phosphate buffer. Illumination used laser light (664nm) at 0.1W for 4 minutes.

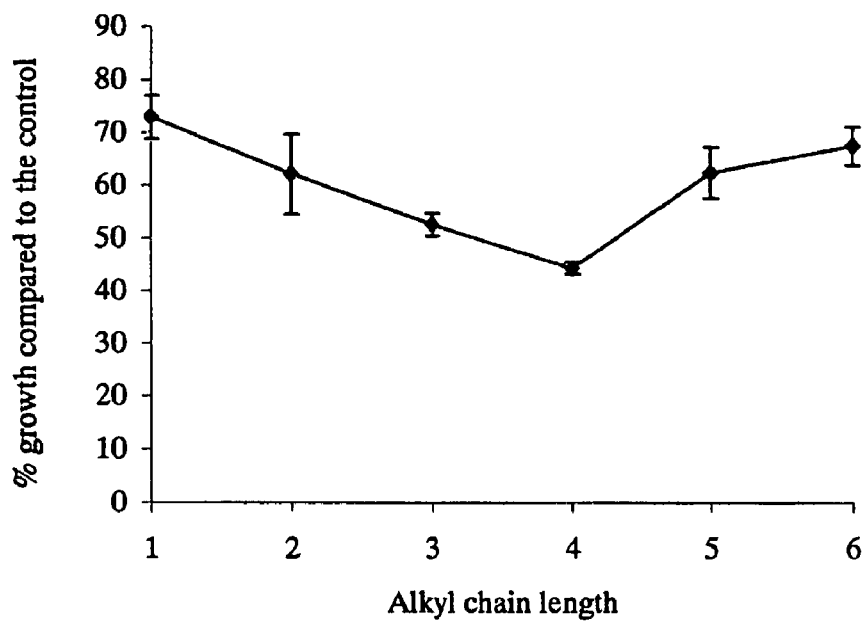
Figure 11 Percentage growth of a culture of an *E.coli* culture as compared to a control when 10μM phenothiazine was included in the growth media. Incubation was carried out in the dark at 37°C for 6 hours. Measurements based on apparent turbidity at 550nm.

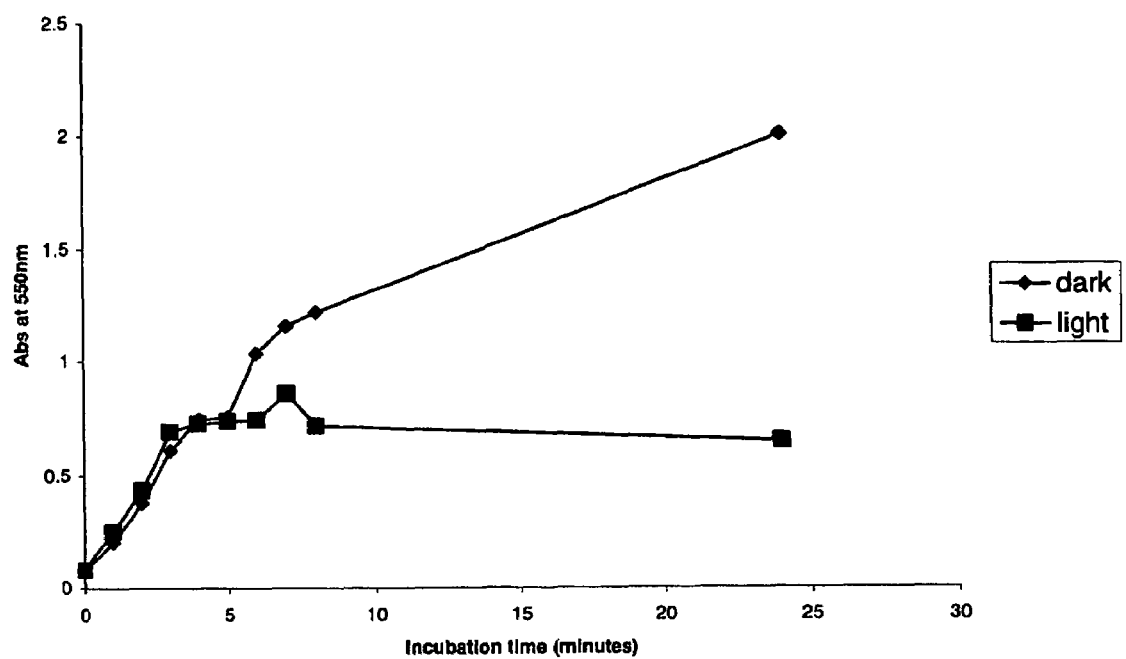
Figure 12 Change in absorbance of an *E.coli* culture grown in the presence of 10μM tetra butyl phenothiazine in the light and in the dark

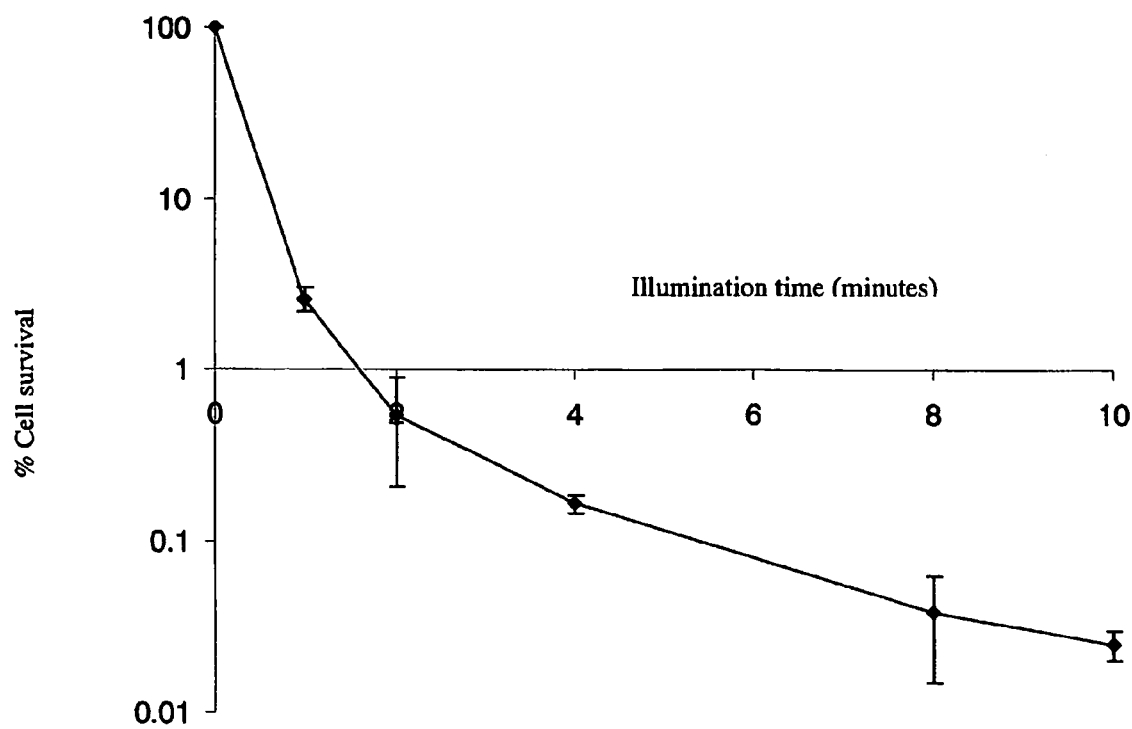
Figure 13 Percentage cell survival of *P.aeruginosa* following incubation with 10μM tetra butyl phenothiazine. Illumination was with laser light (664nm) at 0.1 W.

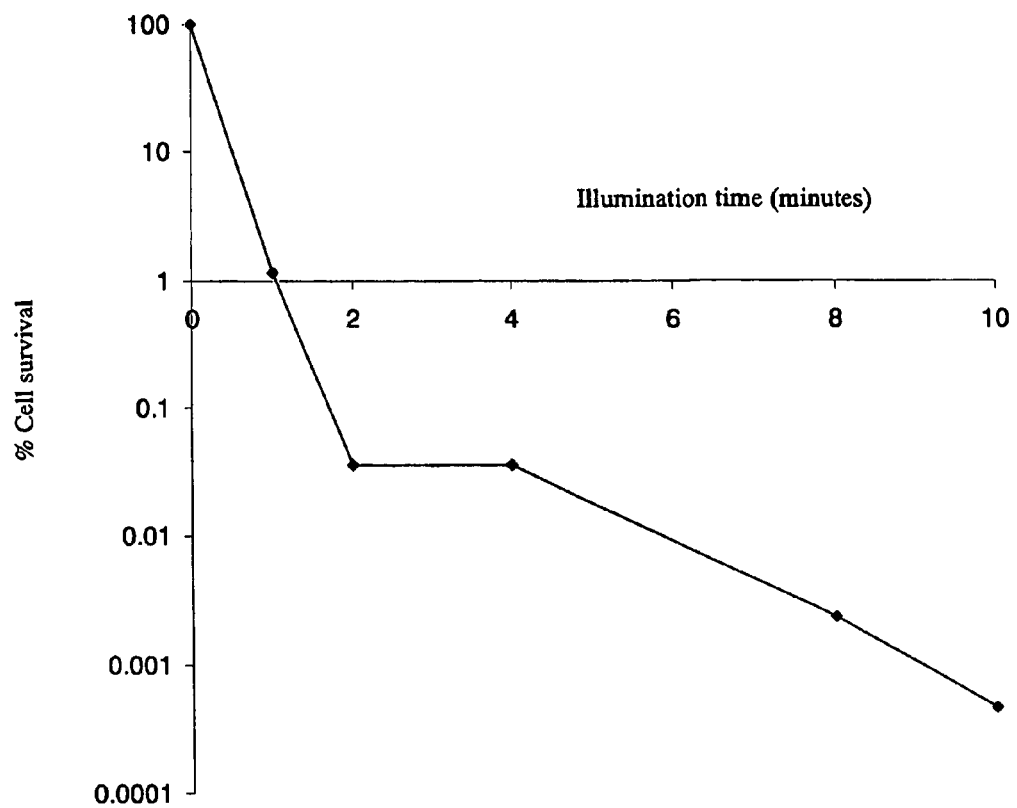
Figure 14 Percentage cell survival of *S.aureus* following incubation with 10µM tetra butyl phenothiazine. Illumination was with laser light (664nm) at 0.1 W.

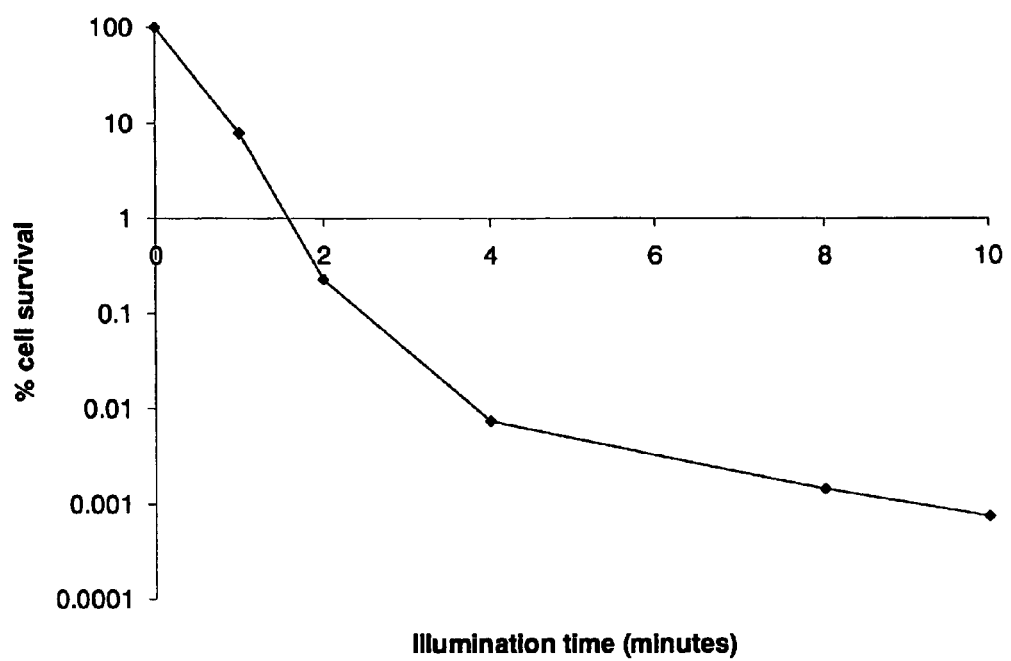
Figure 15 Percentage cell survival of MRSA following incubation with 10μM tetra butyl phenothiazine. Illumination was with laser light (664nm) at 0.1W

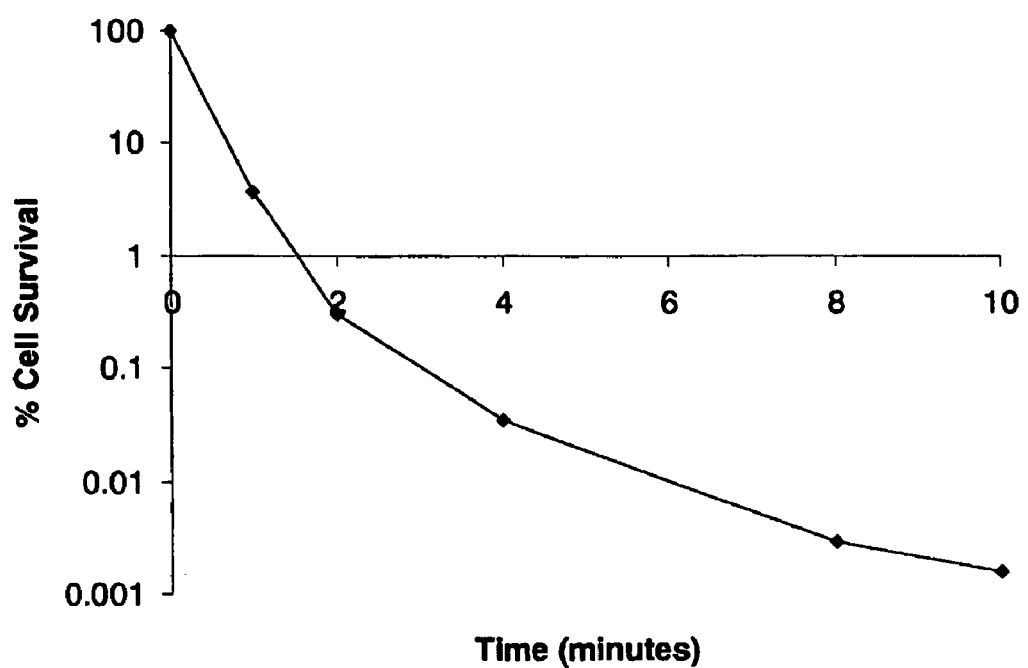
Figure 16 Percentage cell survival of *C.albicans* following incubation with 10μM tetra butyl phenothiazine. Illumination was with laser light (664nm) at 0.1W Figure 17
Protocol:
Drug applied topically, dose = 5.79 μg (20μl at 0.5mM)
Applied light dose = 25J/cm² (30mW/cm² for 831sec)

| | |
|---|---|
| 1 | PHP (i.v.) 8.35 μmol/kg 24h drug to light interval (solar simulator) |
| 2 | PHP (i.v.) 8.35 μmol/kg 2wk drug to light interval (solar simulator) |
| 3 | Butyl phenothiazinium drug only for 30min |
| 4 | 24h ROOM LIGHT + Butyl phenothiazinium |
| 5 | 24h ROOM LIGHT |
| 6 | 24h DARK + Butyl phenothiazinium |
| 7 | 24h DARK |
| 8 | Butyl phenothiazinium 30min drug to light interval (660±15nm) |
| 9 | Butyl phenothiazinium 30min drug to light interval (solar simulator) |
| 10 | Butyl phenothiazinium 24h drug to light interval (solar simulator) |
| 11 | Butyl phenothiazinium 7 days drug to light interval (solar simulator) |
| 12 | Butyl phenothiazinium 14 days drug to light interval (solar simulator) |

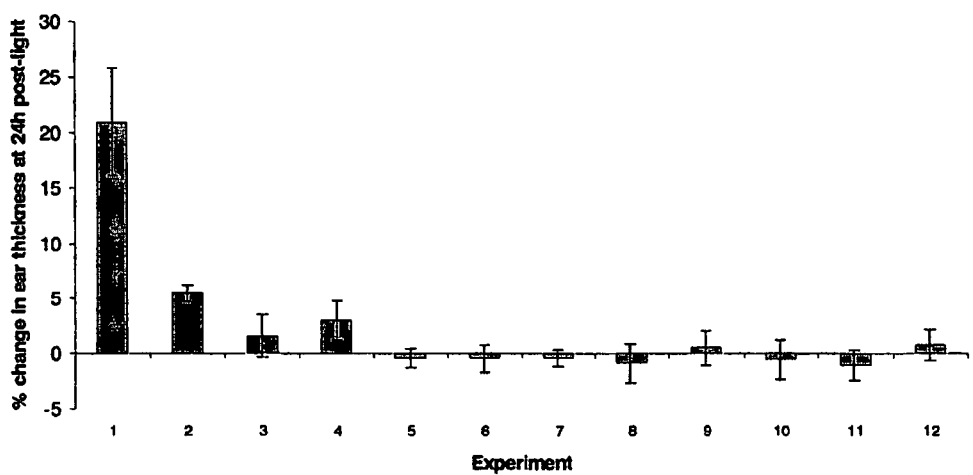

BIOLOGICALLY ACTIVE METHYLENE BLUE DERIVATIVES

This is a continuation-in-part of application serial no. PCT/GB02/02278, filed May 30, 2002, which claims priority from Great Britain application Serial No. 0113121.8 filed on May 30, 2001 and Great Britain application Serial No. 0123945.8 filed Oct. 5, 2001.

FIELD OF THE INVENTION

This invention relates to biologically active photosensitisers their conjugates, composites and compositions which are strongly photocytotoxic and have application in the areas of photodynamic therapy (PDT), as well as for the treatment, diagnosis and detection of medical conditions and related uses in photochemical internalisation, in the production of cancer vaccines, in the treatment and prevention of microbial infections and in photodisinfection or photosterilisation.

BACKGROUND TO THE INVENTION

It is known that certain organic compounds ("photosensitisers") can induce cell death by absorption of light in the presence of oxygen. The cytotoxic effect involves Type I and/or Type II photooxidation. Such photosensitisers find use in the treatment of cancer and other diseases or infections with light (photodynamic therapy) and in the sterilisation (including disinfection) of surfaces and fluids by the light-induced destruction of microbes. In this context, the term sterilisation is taken to mean the reduction or elimination of microbes in a particular situation. For prevention of wound infections sterilisation means a significant reduction in bacterial load on, in or around a wound site which helps to promote efficient wound healing or which minimises the chance that wound infection will occur.

It is also known that certain coloured phenothiazinium compounds, (e.g. methylene blue) can take part in Type I and Type II photooxidation processes, but compounds of this type thus far have proved unsuitable or of low efficacy as sensitisers for photodynamic therapy, or have shown low photochemical antimicrobial activity. For application in PDT, a good sensitiser must have at least some and preferably all of the following properties. Most importantly, it should cause the destruction of target cells (for example tumour cells or bacterial cells) efficiently on exposure to light (preferably wavelengths ca. 600-800 nm). The PDT treatment using the photosensitiser should show a high degree of selectivity between target and normal tissues. The sensitiser should have relatively little dark toxicity and it should cause little or no skin photosensitivity in the patient. The sensitiser should have short drug to light intervals for patient and hospital convenience and to minimise treatment costs.

For applications in photosterilisation, a good sensitiser must show a strong phototoxic effect in a wide range of microrganisms, ideally using ambient light, and should not photobleach readily.

In oncology, several different types of photosensitiser have been used to treat both solid tumours and thin tumours of hollow organs such as the oesophagus and bladder. However, the use of these photosensitisers has been restricted partly because of lack of selectivity between tumour and healthy tissue and partly because of the prolonged skin photosensitivity which can be caused. There is a need for new photosensitisers which cause little or no skin photosensitivity and which selectively destroy tumour cells.

Although PDT has previously been used in the treatment of tumours, it has not yet been used clinically against infections caused by bacteria and other microorganisms. The use of antibiotics to treat bacterial infections is becoming challenging due to the increasing resistance of many bacterial species to commonly used antibiotics, such as tetracyclines and beta-lactams. Hospital-acquired antibiotic resistant infections such as MRSA are especially problematic. Photodynamic antibacterial treatment is a promising alternative to antibiotics for local treatment.

When developing antibacterial agents a major problem which must be overcome is the uptake of the drug into the bacterial cell. Gram negative and Gram positive bacteria differ in the composition of their outer surface and respond differently to antimicrobial agents, especially in terms of uptake. Due to the high negatively charged surface of Gram negative bacteria they are relatively impermeable to neutral or anionic drugs, including most commonly used photosensitisers. Development of antimicrobial photosensitisers which are effective against Gram negative bacteria, as well as Gram positive bacteria would be highly beneficial to replace commonly used antibiotics and drugs which are becoming increasingly ineffective due to resistance. A number of different types of photosensitiser have been investigated in bacteria. These include phenothiazinium compounds, phthalocyanines, chlorins and naturally occurring photosensitisers. For uptake into Gram negative bacteria, it is accepted that the cationic derivatives are the most effective.

Phenothiazinium compounds are blue dyes with maximum absorption at wavelengths between 600-700 nm. They have been studied for their non-photodynamic antibacterial properties but few apart from methylene blue and toluidine blue have been investigated photodynamically.

Wainwright et al (1998) investigated the effect of a series of phenothiazinium methylene blue derivatives in tumour cell lines and bacteria. New methylene blue (NMB) and di methyl methylene blue (DMMB) were effective at inactivating MRSA and were shown to be more effective photosensitisers than methylene blue when acting on pigmented melanoma cell lines. Wagner et al (1998) studied these dyes and in addition a hydrophobic derivative for the inactivation of enveloped viruses.

The precise mode of antibacterial action of methylene blue is unknown, but one hypothesis is that because of its stereochemistry it can intercalate into DNA, and that photodynamic action causes DNA damage. Methylene blue itself has been shown to be ineffective as an anti-tumour agent. In addition, methylene blue is known to be susceptible to photobleaching, which could be a serious disadvantage in some applications. Because of the recognised limitations of methylene blue, both anti-tumour PDT and antimicrobial PDT would benefit from development of new phenothiazinium-based photosensitisers.

SUMMARY OF THE INVENTION

According the present invention there is provided a phenothiazinium compound of Formula (I):

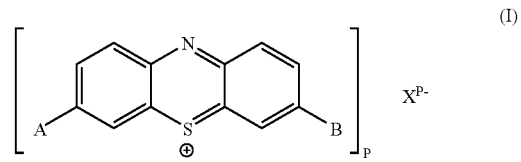

wherein:

A and B each independently is

in which

R' and R" each independently is an optionally substituted linear, branched or cyclic hydrocarbon group, or R' and R" together with the N atom to which they are attached form an optionally substituted 5-, 6- or 7-membered ring;

$X^{P-}$ is a counteranion and P is 1, 2 or 3;

except for the compounds in which A and B are both —$N(CH_3)_2$, or —$N(CH_2CH_3)_2$ for use in a treatment that requires removal, deactivation or killing of unwanted tissues or cells.

The linear and branched chain hydrocarbon groups represented by R' and R" contain from 1 to 12 carbon atoms, preferably from 1 to 10, more preferably from 2 to 8, and especially from 2 to 6 carbon atoms. These linear and branched chain hydrocarbon groups may include one or more unsaturated links, for example one or more alkene groups, and may be optionally substituted by a group selected from H, F, Cl, Br, I, —OH, —$OC_{1-6}$-alkyl, —CN, —$OCOC_{1-6}$-alkyl or aryl. These linear and branched chain hydrocarbon groups are preferably unsubstituted and are preferably saturated hydrocarbon groups.

The cyclic hydrocarbon groups represented by R' and R" contain from 3 to 8 carbon atoms, preferably from 4 to 6 carbon atoms and more preferably 6 carbon atoms. These cyclic hydrocarbon groups may include one or more unsaturated links, they may be optionally substituted and may optionally include a heteroatom such as nitrogen.

Where R' and R" together with the N atom to which they are attached form an optionally substituted 5-, 6- or 7-membered ring the ring may contain other heteroatoms and may be optionally substituted. The heteroatoms are preferably selected from N, O or S. The heteroatoms may be substituted by O, H or $C_{1-6}$-alkyl which is optionally substituted by —OH or —$COCH_3$, preferred substituted heteroatoms are selected from $SO_2$, NH, $NCH_3$, $NC_2H_5$, $NCH_2CH_2OH$ and $NCOCH_3$. The optional ring substituents may be selected from —$C_{1-6}$-alkyl, —OH, —$OC_{1-6}$-alkyl, —OC $OC_{1-6}$-alkyl.

The counteranion represented by $X^{P-}$ may be an organic or inorganic counteranion and is preferably selected from $F^-$, $Br^-Cl^-$, $I^-$, $NO_3^-$, $SCN^-$, $ClO_3^-$, $ClO_4^-$, $IO_3^-$, $BF_4^-$, $HSO_4^-$, $H_2PO_4^-$, $CH_3SO_4^-$, $N_3^-$, $SO_4^{2-}$, $HPO_4^{2-}$, $PO_4^{3-}$, acetate, lactate, citrate, tartrate, glycolate, glycerate, glutamate, β-hydroxyglutamate, glucouronate, gluconate, malate and aspartate.

In a preferred embodiment in the compounds of Formula I A and B each independently is selected from

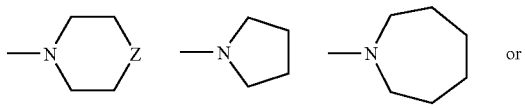

-continued

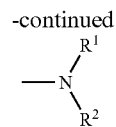

in which Z is $CH_2$, $CH_2$—$C_{1-6}$-alkyl, O, S, $SO_2$, NH, $NCH_3$, $NC_2H_5$, $NCH_2CH_2OH$, or $NCOCH_3$ and $R^1$ and $R^2$ each independently is linear or branched —$C_nH_{2n}Y$, where n is 1-10, preferably 1-8 and more preferably 1-6, Y is H, F, Cl, Br, I, —OH, —$OCH_3$, —$OC_2H_5$, —$OC_3H_7$, —CN, —$OCOCH_3$ or phenyl, or $R^1$ and $R^2$ each independently is cyclohexyl, and in which each of the 5-, 6- or 7-membered rings above may carry one or more —$C_{1-6}$-alkyl, preferably —$C_{1-4}$-alkyl substituents and where $X^{P-}$ is a counteranion and P is 1, 2 or 3.

In a further preferred embodiment $R^1$ and $R^2$ each independently is a linear or branched unsubstituted $C_{1-12}$ alkyl group or a group —$C_nH_{2n}Y$, where n is 1-6, Y is H, F, Cl, Br, I, —OH, —$OCH_3$, —$OC_2H_5$, —$OC_3H_7$, —CN or —$OCOCH_3$, or $R^1$ and $R^2$ each independently is cyclohexyl, or A and B each independently is selected from pyrrolidino or piperidino. More preferably Y is H, F, Cl, Br, I, —$OCH_3$, —$OC_2H_5$, —$OC_3H_7$, —CN or —$OCOCH_3$, Preferably the counteranion is selected from the group comprising $Cl^-$, $Br^-$, $I^-$, $F^-$, $NO_3^-$, $HSO_4^-$, $CH_3CO_2^-$, or a dianion, namely, $SO_4^{2-}$ or $HPO_4^{2-}$, or a trianion namely $PO_4^{3-}$ or from the group comprising $Cl^-$, $Br^-$, $I^-$, acetate, lactate, citrate, tartrate, glycolate, glycerate, glutamate, β-hydroxyglutamate, glucouronate, gluconate, malate, aspartate, and more preferably from the group comprising $Cl^-$, $Br^-$, $I^-$.

In a preferred sub-group of compounds of Formula I A and B are both —$NR^1R^2$ groups and these may be the same or different and $R^1$ and $R^2$ are selected independently from ethyl, n-propyl, n-butyl, i-butyl, n-pentyl, i-pentyl, n-hexyl, $HO(CH_2)_2$—, 2-ethylpiperidino, 2-methylpyrrolidino and cyclohexyl. In this preferred sub-group it is further preferred that when $R^1$ and $R^2$ are both $HO(CH_2)_2$— in the A group that $R^1$ and $R^2$ in the B group are both n-Pent.

In a further preferred sub-group of compounds of Formula I A and B may be the same or different and $R^1$ and $R^2$ are selected independently from ethyl, n-propyl, n-butyl, i-butyl, n-pentyl, i-pentyl, n-hexyl, 2-ethylpiperidino, 2-methylpyrrolidino and cyclohexyl.

In a further preferred sub-group of compounds of Formula I A and B may be the same or different and $R^1$ and $R^2$ are selected independently from ethyl, n-butyl, i-butyl, n-pentyl, i-pentyl, n-hexyl, 2-ethylpiperidino, 2-methylpyrrolidino and cyclohexyl.

In a further preferred sub-group of compounds of Formula I A and B may be the same or different and the sum of the carbon atoms in the alkyl side chains represented by $R^1$ and $R^2$ is from 14 to 40, preferably from 16 to 36, and more preferably from 18 to 30, and especially from 18 to 24.

In a further preferred sub group of compounds of Formula I A and B may be the same or different and the sum of the carbon atoms in the alkyl side chains represented by $R^1$ and $R^2$ is from 16 to 20 preferably from 18 to 20, In one embodiment preferably A and B are the same and both $R^1$ and $R^2$ are n-propyl, n-butyl or n-pentyl.

In a further embodiment A and B are preferably different and $R^1$ and $R^2$ are the same or different, preferably selected from n-propyl, n-butyl, n-pentyl, n-hexyl, n-octyl, 2-methylpyrrolidino, 2-ethylpiperidino, and morpholino.

Especially preferred moieties for use in treatments that require removal, deactivation or killing of unwanted tissues or cells are as follows:

3,7-(tetra-n-propylamino)-phenothiazin-5-ium;
3,7-(tetra-n-butylamino)-phenothiazin-5-ium;
3,7-(tetra-n-pentylamino)-phenothiazin-5-ium;
3,7-(tetra-iso-pentylamino)-phenothiazin-5-ium;
3-(N,N-di-n-butylamino)-7-(N,N-di-n-propylamino)-phenothiazin-5-ium;
3-(N,N-di-n-hexylamino)-7-(N,N-di-n-propylamino)-phenothiazin-5-ium;
3-(2-ethylpiperidino)-7-(N,N-di-n-pentylamino)-phenothiazin-5-ium;
3-(2-methylpyrrolidino)-7-(N,N-di-n-pentylamino)-phenothiazin-5-ium;
3,7-(N,N-tetra-iso-butylamino)-phenothiazin-5-ium;
3-(N,N-di-n-butylamino)-7-(N,N-di-iso-pentylamino)-phenothiazin-5-ium;
3-(N,N-diethanolamino)-7-(N,N-di-n-pentylamino)-phenothiazin-5-ium;
3-(N,N-diethylamino)-7-(N,N-di-n-propylamino)-phenothiazin-5-ium;
3-(N,N-di-n-pentylamino)-7-(N,N-di-n-propylamino)-phenothiazin-5-ium;
3-(N,N-di-n-butylamino)-7-(N,N-di-n-pentylamino)-phenothiazin-5-ium; and
3-((N-ethyl-N-cyclohexyl) amino)-7((-N-ethyl)-N-cyclohexyl) amino-phenothiazin-5-ium. These compounds preferably include a halide as a counteranion which is preferably Cl$^-$, Br$^-$ or I$^-$.

BRIEF DESCRIPTION OF THE DRAWINGS

FIG. 1 is a graph showing percent cross sectional tumour necrosis at 72 hours post-PDT;

FIG. 2 is a graph showing the area of tumour necrosis at 72 hours after PDT with tetra-n-propyl and tetra-n-pentyl derivative;

FIG. 3 is a bar chart depicting the percent change in ear thickness for PHP, butyl and pentyl;

FIG. 4 is a graph of Log change in CFU/ml of *E. coli* incubated for 30 minutes with 10 μM phenothiazine and illuminated for 60 minutes at 1.3 mW/cm$^{-2}$;

FIG. 5 is a graph of Log change in CFU/ml of *E. coli* incubated for 30 minutes with different concentrations of tetra butyl phenothiazine and illuminated for 15 minutes at 1.3 mW/cm$^{-2}$;

FIG. 6 is a graph of Log change in CFU/ml of *E. coli* in the stationary phase of growth following incubation for 30 minutes with 10 μM phenothiazine and illuminated for 60 minutes at 1.3 mWcm$^{-2}$;

FIG. 7 is a Log change in CFU/ml of *E. coli* resuspended in nutrient media, wherein the cells were incubated for 30 minutes with 10 μM phenothiazine and illuminated for 60 minutes at 1.3 mW/cm$^{-2}$;

FIG. 8 is a Log change in CFU/ml of *E. coli* following incubation with 10 μM phenothiazine for 30 minutes;

FIG. 9 is a bar chart of uptake of 120 μM phenothiazine into *E. coli* cells following a 30 minute incubation versus alkyl chain length;

FIG. 10 is a bar chart depicting Log change in CFU/ml of *E. coli* cells incubated with 10 μM pH7 tetra butyl phenothiazine for both washed and unwashed;

FIG. 11 is a graph depicting percentage growth of a culture of an *E. coli* culture as compared to a control when 10 μM phenothiazine was included in the growth media;

FIG. 12 is a graph depicting change in absorbance of an *E. coli* culture grown in the presence of 10 μM tetra butyl phenothiazine in the light and in the dark;

FIG. 13 is a graph depicting percentage cell survival of *P. aeruginosa* following incubation with 10 μM tetra butyl phenothiazine;

FIG. 14 is a graph depicting percentage cell survival of *S. aureaus* following incubation with 10 μM tetra butyl phenothiazine;

FIG. 15 is a graph depicting percentage cell survival of MRSA following incubation with 10 μM tetra butyl phenothiazine;

FIG. 16 is a graph depicting percentage cell survival of *C. albicans* following incubation with 10 μM tetra butyl phenothiazine; and FIG. 17 is graph depicting the percentage change in ear thickness at 24 hours post-light.

DETAILED DESCRIPTION OF THE PREFERRED EMBODIMENT

The phenothiazinium compounds used in the present inventions were synthesised in Leeds University Department of Colour Chemistry under the direction of J. Griffiths.

In outline the phenothiazines of Formula I may be synthesised as follows:

1) Symmetrical Phenothiazinium Compounds where A=B
   a) Phenothiazine is firstly brominated with bromine in glacial acetic acid to give 3,7-dibromophenothiazin-5-ium bromide, the suspension formed is collected by filtration.
   b) the 3,7-dibromophenothiazin-5-ium bromide is added to an amine represented by R'R"NH (in which R' and R" are as defined above) or N-heterocycle in chloroform. The solid formed is collected by filtration and purified for example by flash column chromatography over silica gel 60, using chloroform, chloroform/methanol (98/2) and then chloroform/methanol (90/10). The product may be further purified by precipitation from chloroform with petroleum ether (b.p. 60-80° C.).

2) Unsymmetrical Phenothiazinium Compounds where A B
   a) Phenothiazine in chloroform is cooled to below 5° C. and a solution of iodine in chloroform added. The solid formed is collected by filtration, washed with chloroform until free of iodine and then kept at room temperature under vacuum overnight to give phenothiazin-5-ium tetraiodide hydrate.
   b) the phenothiazin-5-ium tetraiodide hydrate in methanol is added to a solution an amine R'R"NH in methanol (in which R' and R" are as defined above). The reaction mixture is stirred overnight, reduced by evaporation left to cool. The solid that formed is collected by filtration, washed with diethyl ether and dried.
   c) triethylamine in dichloromethane followed by a solution of a different second amine R'R"NH (in which R' and R" are as defined above) in dichloromethane is added to a solution of the solid from b) above in dichloromethane. The reaction mixture is stirred overnight, the organic layer washed with dilute hydrochloric acid and water, separated and dried (MgSO$_4$). The majority of the solvent is evaporation and diethyl ether added to precipitate the product which is collected by filtration, washed with diethyl ether and dried. Further purification of the product, if necessary, may be by flash column chromatography.

The present invention also provides compositions comprising a compound of Formula I together with a diluent or excipient. Further compositions of the present invention include those comprising two or more compounds of Formula I and those comprising one or more compounds of Formula I with one or more different therapeutic or active agents.

The compounds of Formula I may be formulated into a variety of pharmaceutical compositions which contain the compounds and pharmaceutically acceptable carriers, excipients, adjuvants (each selected for certain characteristics that permit optimal formulation of a pharmaceutical composition). The compositions include liposomes, nanoparticles, colloidal suspensions, micelles, microemulsions, vesicles and nanospheres.

The compositions may also comprise further components such as conventional delivery vehicles and excipients including solvents such as alcohols (for example ethanol, polyethylene glycol, glycerol or n-butanol), dimethyl sulphoxide, water, saline, solubilisers such as castor oil derivatives for example ethoxylated castor oils like Cremophor EL (trade mark BASF AG) or Tween (trade mark, ICI Americas Inc.) types, isotonising agents such as urea, glycerol, aminoethanol, propylene glycol, pH regulators, dyes, gelling agents, thickeners, buffers, and combinations thereof.

Typically the compositions are prepared by mixing a compound of Formula I with one or more pharmaceutically acceptable carriers at an appropriate temperature, typically from 15° to 65° C. at an appropriate pH, typically from pH 3 to 9 and preferably at a physiologically acceptable pH such as from pH 6.5 to 7.5.

The concentration of the compounds of the present invention in the compositions depends on the compound's photosensitising ability and is preferably in the range from 0.0005 to 20% for topical use and from 100 µM to 30 mM for intravenous use. Dry compositions, which may be reconstituted before use, are also provided in the present invention. These may be prepared by dry mixing solid components of the composition or preparing a liquid composition which is evaporated to dryness generally under mild conditions under vacuum or in low temperature ovens.

According to a further feature of the present invention the compounds of Formula I have many uses, particularly in the treatment of infection and cancer; the treatment of dermatological, ophthalmic, cardiovascular, gynaecological and dental conditions; and the prevention of infection, The uses may be in humans or animals. The present compounds may be used against microorganisms.

In one embodiment of the present invention a compound of Formula I is used as a PDT agent or a photodiagnostic agent.

In one embodiment of the present invention compounds of Formula I and compositions comprising them are used as medicaments particularly as anticancer agents, as antibacterials, antifungals and antivirals.

Examples of uses of the compounds of the present invention are as photosensitising drugs for PDT to treat cancer and pre-cancerous conditions including Barrett's oesophagus and cervical intraepithelial neoplasia (CIN), bladder cancer, colon cancer, non-melanoma skin cancer, actinic keratoses, melanoma, brain-pituitary cancer, brain-glioma, pancreatic cancer, head and neck cancer, lung cancer, particularly non small cell, mesothelioma, oesophageal cancer, stomach cancer, cutaneous T-cell lymphoma; to treat infections, for example for use as anti-microbial and antifungal treatments for skin and wound infections such as burn wounds, in treatment of ulcers particularly leg ulcers more particularly infected chronic leg ulcers, nail infections; for parasitic infection, stomach infection, malaria, leprosy, for bacterial and fungal spore inactivation, for treatment of prions and viral infection such as HIV, for ear, nose and throat infections, tuberculosis, sexually transmitted diseases (STD's), herpes, for treatment of Candida localised infections for example of hair, nails and epidermis, such as tinea pedis and candida vulvovaginitis; and for use as infection preventatives such as sterilisation of surgical wounds, skin graft sterilisation, stem cell sterilisation, graft versus host disease; to treat ophthalmological conditions such as macular degeneration, occult choroidal neovascularisation (CNV), CNV due to pathological myopia, occult with age related macular degeneration (AMD), diabetic macular oedema, vascular problems such as cardiovascular disease, arteriosclerosis and restenosis and autoimmune diseases such as rheumatoid arthritis, skin diseases such as psoriasis, acne, vitiligo and eczema and other dermatological conditions such as hirsuitism, and sun damage, other benign conditions such as endometriosis and menorrhagia.

The compounds may also be used for other local infections as well as in the treatment of dental bacterial disease, such as gum abscesses, gum disease, gingivitis, and removal, deactivation or killing of plaque biofilms. The compounds may also be used in photochemical internalisation (the use of photosensitisers to assist the uptake and subcellular localisation of drugs) through their photosensitising properties and in non-therapeutic uses such as in photodiagnosis through their fluorescence properties. The latter approach takes advantage of the fact that the photosensitiser concentrates more in tumours than in surrounding healthy tissue and when induced to fluoresce (by application of blue light), the tumour fluoresces more strongly than the surrounding tissue. Examples of applications areas include diagnoses for oral diseases and for diseases of the bladder, lung and skin.

In addition to the above the present compounds are used as photosensitising drugs for PDT in veterinary applications, for example in treatment of cancers such as ear cancer in cats, as antifungal, antibacterial and antviral treatments, for sterilisation of wounds in animals and for ophthalmological treatments in animals.

The use of the compounds of Fomula I is preferably in treatments of localised and/or early cancer and/or pre-cancerous lesions in humans and in animals; or in the treatment and/or prevention of infections in wounds or skin in humans and animals. According to a further feature of the present invention the present compounds may be used as photoactivated antimicrobial, antifungal and antiviral agents for sterilisation of surfaces and fluids, for example they may be used to sterilise surgical implants and stents, particularly where these are coated or impregnated, to sterilise textiles such as bandages and dressings, IV lines and catheters, for sterilisation of water, air, blood, blood products, and food and food packaging to prevent transfer of infection, and for general household, hospital and office cleaning. The compounds are preferably used to sterilise surgical implants and stents, particularly where these are coated or impregnated, to sterilise textiles such as bandages and dressings, IV lines and catheters, for sterilisation of water, air, and food and food packaging to prevent transfer of infection, and for general household, hospital and office cleaning. The compounds may be applied to or contacted with the surfaces and fluids and activating the compound by exposure to light. Additionally the surface to be sterilised may be immersed in a mixture or solution of the compound or the fluid to be sterilised may be mixed with the compound or a solution or mixture containing the compound.

The present invention relates to phenothiazinium sensitizers which show an unexpected and pronounced dependence of their photobiological properties in vitro and in vivo on the size and hydrophobic character of substituents on the terminal amino groups. By careful selection of such structural features, photosensitisers with distinct advantages over existing materials are provided. Accordingly compounds of the present invention overcome the problems of the prior art by providing the following advantages in the field of oncology and in their antimicrobial effects:

Advantages in Oncology
  Extremely strong photoactivity when compared with methylene and ethylene blue.
  Low absorption of light in the UV/blue region. This results in a lower propensity of the compounds to skin photosensitivity.
  Rapid skin clearance.
  High selectivity for tumours.
  Low dark toxicity.
  Low potential for DNA damage when compared with methylene blue.
  Very short drug-to-light time interval compared with existing PDT drugs.

Antimicrobial Advantages
  Highly effective in deactivating a wide range of microorganisms, including Gram positive and Gram negative bacteria, MRSA and fungal infection.
  Active against quiescent/stationary bacteria.
  High selectivity for microorganisms with minimum damage to host tissue.
  Unexpectedly low level of photobleaching.

In any of the uses described above the compounds of the present invention may be used advantageously in mixtures comprising two or more compounds of Formula I and in mixtures comprising one or more compounds of Formula I with one or more different therapeutic or active agents.

The compounds of the present invention are particularly useful as photosensitising drugs for PDT of conditions where treatment requires removal, deactivation or killing of unwanted tissue or cells such as cancer, precancerous disease, ophthalmic disease, vascular disease, autoimmune disease, and proliferative conditions of the skin and other organs. Specific and unpredicted advantages of these materials relate to their ability to be photoactive against target tissues at different times after systemic administration (depending upon the particular sensitiser used) and therefore their ability to be targeted directly for example to the vasculature or tumour cells. They also have a low tendency to sensitise skin to ambient light when administered systemically and a low tendency to colour skin.

Accordingly, the present invention provides a method of treatment for cancer and other human or animal diseases through systemic or local administration of the photosensitiser, followed by application of light of an appropriate dose and wavelength or wavelength range.

For the present compounds activation is by light, including white light, of an appropriate wavelength, usually in the range from 600 to 800 nm, preferred wavelengths are from 630 nm to 700 nm.

The light source may be any appropriate light source such as a laser, laser diode or non-coherent light source.

The light dose administered during PDT can vary but preferably is from 1 to 200 J/cm$^2$, more preferably from 20 to 100 J/cm$^2$.

Light exposure may be given at any time after a drug is initially administered or up to 48 hours after drug administration and the time may be tailored according to the condition being treated, the method of drug delivery and the specific compound of Formula (I) used. Light exposure is preferably given at any time after a drug is initially administered up to 3 hours, more preferably from the time after a drug is initially administered up to 1 hour, especially up to 10 minutes.

Increased intensity of the light dose generally reduces exposure times.

It is preferred that exposure to light is localised to the area/region to be treated, and where tumours are being treated more preferably localised to the tumour itself.

In one embodiment of the present invention the compound is preferably administered to a subject in need of treatment is that according to formula (I), where $R^1$ and $R^2$ are n-propyl and said light exposure is given up to 10 minutes after a drug is initially administered.

In a further preferred embodiment of the invention, light exposure is given within 1 minute after a drug is initially administered.

More preferably light exposure is given at the point of drug administration.

Where the compound administered is that according to Formula (I), where $R^1$ and $R^2$ are n-pentyl said light exposure is given at longer times, for example up to 60 minutes after a drug is initially administered.

Where the compounds of the present invention are used as PDT agents for mammalian cells and tumours they may be administered using the above described compositions in a variety of ways, such as systemically or locally and may be used alone or as components or mixtures with other components and drugs. Where administered systemically the compounds may be delivered for example intravenously, orally, sub-cutaneously, intramuscularly, directly into affected tissues and organs, intraperitoneally, directly into tumours, intradermally or via an implant. Where administered locally or topically the compounds may be delivered via a variety of means for example via a spray, lotion, suspension, emulsion, gel, ointment, salves, sticks, soaps, liquid aerosols, powder aerosols, drops or paste.

The compounds of the present invention have the advantage, compared with other phenothiazinium photosensitisers, that they do not, in carrying out their cell-destroying activity, target the nucleus of the cell so that there is a much lower risk of the cells undergoing mutagenic transformations.

The dose rates of the compounds of Formula I for intravenous administration to humans for oncology treatments are in the range 0.01 to 10 µmol (micromole)/kg, preferably in the range 0.1 to 2.0 µmol (micromole)/kg. To achieve a dose of say 2 µmol (micromole)/kg in a 70 kg patient requires injection of 70 ml of a 2 mM solution, or 5 ml at a concentration of 27 mM (16 mg/ml) or 2.8 ml of a 50 mM solution. Typical injections volumes are in the range 0.1 to 100 ml, preferably from 5 to 50 ml.

In one embodiment the method for treatment of cancer comprises the step of administering a compound according to Formula (I) where $R^1$ and $R^2$ are selected independently from ethyl, n-propyl, n-butyl, i-butyl, n-pentyl, i-pentyl, n-hexyl, 2-ethylpiperidino, 2-methylpyrrolidino and HO(CH$_2$)$_2$, preferably where $R^1$ and $R^2$ are selected independently from ethyl, n-propyl, n-butyl, i-butyl, n-pentyl, i-pentyl, n-hexyl, 2-ethylpiperidino and 2-methylpyrrolidino.

In a further feature of the present invention the compounds of Formula I preferably are used against bacteria, more preferably the compounds are used against antibiotic resistant bacteria.

The compounds may also be used in PDT as photoactivatable antimicrobials, including antibacterials, antifungals or antivirals, treatments for skin and other local infections, for sterilisation of burn wounds and other lesions, for sterilisation of both recipient tissue and donated tissue during organ, including skin, transplantation and for the treatment of dental microbial disease.

The said compounds are also useful as photoactivatable antimicrobial agents for general sterilisation of surfaces and fluids. Specific advantages of these compounds over existing known antimicrobial photosensitisers are their high photocytotoxicity at low light levels, combined with a low tendency to undergo photobleaching.

According to a further feature of the present invention there is provided a method of treatment of microbial infections, burn wounds and other lesions and of dental bacterial disease, the method comprising systemic administration or applying to the area to be treated (for example by a spray, lotion, suspension, emulsion, ointment, gel or paste) a therapeutically effective amount of a compound of the present invention and exposing said area to light to render active said compound.

In one embodiment the method comprises the step of administering a compound according to Formula I in which A and B are both —$NR^1R^2$ groups and these may be the same or different where $R^1$ and $R^2$ are selected independently from ethyl, n-propyl, n-butyl, n-pentyl, i-pentyl, n-hexyl, 2-ethylpiperidino, 2-methylpyrrolidino and cyclohexyl.

In a further embodiment the method comprises the step of administering a compound according to Formula (I) in which A and B are both —$NR^1R^2$ groups where $R^1$ and $R^2$ are n-butyl or n-pentyl.

According to a further feature of the present invention there is provided a method of prevention of microbial infections, for example in wounds, surgical incisions, burn wounds, and other lesions and of dental bacterial disease, the method comprising systemic administration or applying to the area to be treated (for example by a spray, lotion, suspension, emulsion, ointment, gel or paste) a therapeutically effective amount of a compound of the present invention and exposing said area to light to render active said compound. The compounds of Formula I may be applied to prevent infection at any stage including wound contamination, where non-replicating organisms are present in a wound; wound colonisation where replicating microorganisms are present in a wound; and wound infection where replicating microorganisms are present that cause injury to the host. When there are >$10^5$ CFU/g tissue, it is more likely that sepsis will develop.

The concentration used for bacterial cell kill in vitro is in the range from 0.1 to 100 μM, preferably from 1 to 50 μM and more preferably from 5 to 20 μM, especially 10 μM.

Furthermore, the present invention provides a conjugate or composite formed between a compound of Formula I and a polymer. The term composite as used herein refers to the situation wherein a compound of the invention is embedded in a polymer or physically occluded within or adsorbed onto a matrix or substrate. The polymer may be a biological polymer such as a peptide or a protein. Preferred polymers include those having anhydride and/or ester groups. Preferred compounds of Formula I which form a conjugate or composite with a polymer are those in which at least one of the Group A or B is a piperazinyl group.

In addition, the present invention provides a compound formed by the reaction between a compound of Formula I and a chlorotriazine derivative. The chlorotriazine derivative may be a polymer having chlorotriazine groups attached thereto.

Appropriate compounds of the present invention may be attached to polymeric surfaces, permanently by covalent bonds or reversibly by intermolecular interactions, thus affording a surface that can be sterilised whenever required by the application of light. This would be useful, for example, with intravenous lines in patients and in sutures and catheters and intravenous lines, where maintaining long-term sterility of the relevant surfaces is problematical. The resistance of the compounds to photobleaching is an advantage in such applications, where prolonged stability of the chromophore is required.

Accordingly the present invention also provides an article having at least one surface to which is attached a compound of the present invention.

Preferably the article is a medical device such as a venous, urinary or balloon catheter, suture, orthopaedic or artifical implant, heart valve, surgical screw or pin, pacemaker lead, feeding or breathing tube, vascular stent, intraocular lens, or small joint replacement. The article may also be of use in wound care and for packaging materials for medical use, for example, materials for medical equipment.

A compound of the present invention may be applied to or contacted with walls, floors and ceilings of hospitals, clinical surfaces such as operating tables, abattoirs, clean rooms in scientific laboratories, fibres which may be converted into woven, knitted or non-woven textile articles such as cleaning cloths, wipes, surgical gowns, bed linen, wound dressings and bandages. The compound may be applied directly or via attachment to a polymeric species.

Where the compound is to be applied to walls, floors, ceilings, and work surfaces, it is envisaged that it will be used as a component of a paint or lacquer, which comprises the compound, film forming polymers, which may or may not be cross-linkable, and an appropriate solvent, optionally with drying agents and other colorants. The surface coating may take the form of a solution or water-based dispersion.

Where compound or polymer is applied to walls, floors, ceilings this may be via a surface coating such as a paint.

Alternatively the article is one for use in the food and beverage industry and may be an item of packaging, a wrapper or storage carton or a piece of processing equipment. The article may be a refrigerator, vending machine, ice making machine, a piece of restaurant equipment or other kitchen appliance.

Furthermore, the present invention also provides a method of sterilising a surface or a fluid comprising contacting or applying the compound of the present invention to said surface or fluid and activating said compound by means of light. The compound may be contacted or applied by any means, for example as a spray, liquid, solution, suspension, foam, cream, gel or emulsion.

According to a further feature of the present invention there is provided a method for sterilising fluids in which the fluid is contacted with a compound of Formula I or with a conjugate or composite formed between a compound of Formula I and a polymer whilst the compound or the conjugate or composite is illuminated.

The fluid may be a liquid or a gas or a vapour. The method may for example be applied to sterilisation of liquids, for example for sterilisation of water, or liquids used medically such as parenteral liquids for example saline or glucose and particularly for sterilisation of biological liquids such as blood, blood products, red cells, bone marrow cells, and stem cells. The method may also be applied to sterilisation of gases such as air, particularly air used in air conditioning systems, and oxygen used medically. This method is particularly useful for sterilising materials which cannot be easily sterilised by filtration methods.

The method is used preferably for sterilisation of water, or liquids used medically such as parenteral liquids such as saline or glucose and for sterilisation of biological liquids such as bone marrow cells and stem cells.

The compounds of Formula I and its conjugates or composites may be used as is, preferably with its surface area maximised such as in a finely divided form or in the form of beads or plates, or it may be used on or associated with any support material which provides a large surface area such as glass, glass wool, ceramics, plastics, metals and metal oxides. The support material is preferably transparent to light or allows light to pass through it. Where a support material is used this is arranged to maximise the surface area covered by the conjugate or composite and may be in the form of beads, plates, large surface areas in columns or tubes, foams or fibres.

The compound of Formula I or its conjugate or composite is preferably continuously illuminated at the wavelengths and at the light doses described above.

The preferred compounds of Formula I are those preferred in this sterilisation method.

In a particular embodiment of this aspect of the invention the compound of Formula I or its conjugate or composite either alone or on a support material is packed into a column, typically made of a material which is transparent to light, such as silica glass or synthetic fibres. The fluid requiring sterilisation is passed into one end of the column, the whole column is continuously illuminated and sterilised material flows out from the other end of the column.

Certain compounds of Formula I wherein:
A and B each independently is

in which R' and R" each independently is a linear, branched or cyclic hydrocarbon group, or R' and R" together with the N atom to which they are attached form an optionally substituted 5-, 6- or 7-membered ring;
and where $X^{p-}$ is a counteranion and P is 1, 2 or 3;
except for the compounds in which A and B are the same and are selected from —N(CH$_3$)$_2$, —N(CH$_2$CH$_3$)$_2$, N(n-Pr)$_2$, —N(n-Bu)$_2$, —N(n-Pent)$_2$, —N(n-Hex)$_2$, —N(n-Hept)$_2$, piperidino, —N(CH$_2$CH$_2$OH)$_2$, —N(diethylhexyl)$_2$,
and not including those in which A is selected from —N(Me)$_2$ or —N(Et)$_2$ and B is selected from —N(CH$_2$CH$_2$OH)$_2$, piperidino, morpholino, thiomorpholino, —N(Et)$_2$, —N(MeEt), —N(Me)$_2$ are novel and accordingly these form a further feature of the present invention. The preferences described above apply to the compounds of Formula I themselves.
Specific novel moieties include:
3-(N,N-di-n-butylamino)-7-(N,N-di-n-propylamino)-phenothiazin-5-ium;
3-(N,N-di-n-hexylamino)-7-(N,N-di-n-propylamino)-phenothiazin-5-ium;
3-(2-ethylpiperidino)-7-(N,N-di-n-pentylamino)-phenothiazin-5-ium;
3-(2-methylpyrrolidino)-7-(N,N-di-n-pentylamino)-phenothiazin-5-ium;
3,7-(N,N-tetra-iso-butylamino)-phenothiazin-5-ium;
3-(N,N-di-n-butylamino)-7-(N,N-di-iso-pentylamino)-phenothiazin-5-ium;
3-(N,N-diethanolamino)-7-(N,N-di-n-pentylamino)-phenothiazin-5-ium;
3-(N,N-diethylamino)-7-(N,N-di-n-propylamino)-phenothiazin-5-ium;
3-(N,N-di-n-pentylamino)-7-(N,N-di-n-propylamino)-phenothiazin-5-ium;
3-(N,N-di-n-butylamino)-7-(N,N-di-n-pentylamino)-phenothiazin-5-ium; and
3-((N-ethyl-N-cyclohexyl) amino)-7((-N-ethyl)-N-cyclohexyl) amino-phenothiazin-5-ium These compounds preferably include a halide as a counteranion which is preferably Cl$^-$, Br$^-$ or I$^-$.

EXAMPLES

1) General Synthesis of Symmetrical Phenothiazinium Bromides of Formula I where (A=B=R'R"N— or A=B=N-heterocycle; p=1, $X^{p-}$=Br$^-$).

a) Preparation of 3,7-dibromophenothiazin-5-ium Bromide

To a solution of phenothiazine (2.00 g, 0.01 mol) (Note 1)in oxygen-free, glacial acetic acid (150 cm$^3$) was added, in one portion and with vigorous stirring, a solution of bromine in oxygen-free, glacial acetic acid (100 cm$^3$, 10% v/v Br$_2$). The reaction mixture became dark with the formation of a dark solid. Stirring was continued for one minute and water (400 cm$^3$) was then added, when the suspension took on a red appearance. The reaction mixture was vacuum filtered to produce a dark solid and a brown filtrate. The solid was washed with ether and dried under vacuum (40° C., 50 mmHg) for one hour to yield a brick red product. Mass of solid=3.63 g Yield=83%.

b) Preparation of the Symmetrical Phenothiazinium Bromides

To a solution of the appropriate amine R'R"NH or N-heterocycle (32.4 mmol) in chloroform (200 cm$^3$) under nitrogen and with vigorous stirring was added, in one portion, 3,7-dibromophenothiazin-5-ium bromide (2.0 g, 4.6 mmol). The reaction mixture became blue in colour and was stirred under nitrogen for 3 hours. The chloroform solution was washed successively with HBr (2% aq., 2×50 cm$^3$) and water (2×50 cm$^3$), and then dried over MgSO$_4$. After filtration, the majority of the solvent was removed by rotary evaporation, an excess of diethyl ether was added and the reaction mixture then left to stand. After some time, a large amount of colourless solid was deposited. This material was removed by filtration. The filtrate was evaporated to dryness and the residual crude product was purified by flash column chromatography over silica gel 60, employing sequentially a mobile phase of chloroform, chloroform/methanol (98/2) and finally chloroform/methanol (90/10). The relevant blue chromatographic fractions were combined and the solvent removed by rotary evaporation. The dark blue product was taken up in a minimum volume of dichloromethane (10 cm$^3$) and the final product precipitated in crystalline form by the addition of an excess of petroleum ether (b.p. 60-80° C.). The solid was collected by filtration, washed with ether and air dried.

The purity of each product was confirmed by thin layer chromatography (showing a single detectable blue spot), and the structure was confirmed by electrospray mass spectrometry and UV/visible absorption spectroscopy).

2) General Synthesis of Unsymmetrical Phenothiazinium Iodides of Formula I where (A≠B=R'R"N or N-heterocycle, p=1, $X^{p-}=I^-$).

a) Preparation of phenothiazin-5-ium Tetraiodide Hydrate

To a stirred solution of phenothiazine (10 mmole) in chloroform (100 cm³) cooled to below 5° C. in an ice bath was added, over 1.5 hours, a solution of iodine (33 mmole) in chloroform (400 cm³). The mixture was stirred for 30 minutes and the resultant precipitate was collected by filtration, washed with chloroform until free of iodine and then kept at room temperature under vacuum overnight to give the product.

b) Preparation of the Unsymmeterical phenothiazin-5-ium Iodides

To a stirred solution of phenothiazin-5-ium tetraiodide hydrate (1.4 mmole) in methanol (300 cm³) was added, dropwise, over a period of 60 minutes a solution of the appropriate amine $R^1R^2NH$ (3.6 mmole) in methanol (50 cm³). The reaction mixture was stirred overnight. The volume of the reaction mixture was then reduced by evaporation and the hot solution left to cool. The solid that formed was collected by filtration, washed with diethyl ether and dried.

c) To a solution of this solid (0.34 mmole) in dichloromethane (100 cm³) was added a solution of triethylamine (0.40 mmole) in dichloromethane (5 cm³) followed by a solution of a different second amine R'R"NH (1.4 mmole) in dichloromethane (50 cm³) over 60 minutes. The reaction mixture was stirred overnight. The organic layer was then washed with dilute hydrochloric acid (4×25 cm³) followed by water (2×25 cm³). The organic layer was then dried (MgSO₄). The majority of the solvent was removed by rotary evaporation and an excess of diethyl ether added to precipitate the solid. The solid was collected by filtration, washed with diethyl ether and dried. Further purification of the compound, if necessary, was by flash column chromatography.

The purity of each product was confirmed by thin layer chromatography (a single detectable blue spot). Structures were confirmed by electrospray mass spectrometry and UV/visible absorption spectroscopy.

The following specific compounds were prepared by the above methods:

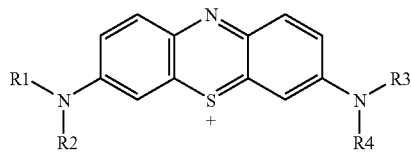

Compound 1 $R^1$-$R^4$=n-$C_3H_7$: tetra-n-propyl
Compound 2 $R^1$-$R^4$=n-$C_4H_9$: tetra-n-butyl
Compound 3 $R^1$-$R^4$=n-$C_5H_{11}$: tetra-n-pentyl
Compound 4 $R^1$-$R^4$=n-$C_6H_{13}$: tetra-n-hexyl
Methylene blue ($R^1$-$R^4$=n-$CH_3$) Compound 5 and ethylene blue ($R^1$-$R^4$=n-$C_2H_5$) Compound 6 were also examined for comparative purposes. Compounds 1 to 6 have iodide counteranions.
Compounds 7, 7a, 8, 8a, 8b and 14-31 were made by analogous methods.

Compound 9 3-(N,N-dimethylamino)-7-(N,N-dipropylamino)-phenothiazin-5-ium iodide (20%)

This compound was obtained following isolation of 3-(N,N-dipropylamino)-phenothiazin-5-ium triiodide and subsequent treatment with dimethylamine hydrochloride. Precipitation from dichloromethane by addition of diethyl ether yielded purple lustrous crystals. Mass spectrometry: $C_{20}H_{26}N_3OS$ requires m/z=340; found m/z=340 ($I^-$ not detected by mass spectrometry).

Compound 10 3-(N,N-diethylamino)-7-(N,N-dipropylamino)-phenothiazin-5-ium iodide (15%)

This compound was obtained following isolation of 3-(N,N-dipropylamino)-phenothiazin-5-ium triiodide and subsequent treatment with diethylamine. Precipitation from dichloromethane by addition of diethyl ether yielded purple lustrous crystals. Mass spectrometry: $C_{22}H_{30}N_3OS$ requires m/z=368; found m/z=368 ($I^-$ not detected by mass spectrometry).

Compound 11 3-(N,N-dibutylamino)-7-(N,N-dipropylamino)-phenothiazin-5-ium iodide (19%)

This compound was obtained following isolation of 3-(N,N-dipropylamino)-phenothiazin-5-ium triiodide and subsequent treatment with dibutylamine. Precipitation from dichloromethane by addition of diethyl ether yielded purple lustrous crystals. Mass spectrometry: $C_{26}H_{38}N_3OS$ requires m/z=424; found m/z=424 ($I^-$ not detected by mass spectrometry).

Compound 12 3-(N,N-dipentylamino)-7-(N,N-dipropylamino)-phenothiazin-5-ium iodide (20%)

This compound was obtained following isolation of 3-(N,N-dipropylamino)-phenothiazin-5-ium triiodide and subsequent treatment with dipentylamine. Precipitation from dichloromethane by addition of diethyl ether yielded purple lustrous crystals. Mass spectrometry: $C_{28}H_{42}N_3OS$ requires m/z=452; found m/z=452 ($I^-$ not detected by mass spectrometry).

Compound 13 3-(N,N-dihexylamino)-7-(N,N-dipropylamino)-phenothiazin-5-ium iodide (22%)

This compound was obtained following isolation of 3-(N,N-dipropylamino)-phenothiazin-5-ium triiodide and subsequent treatment with dihexylamine. Precipitation from dichloromethane by addition of diethyl ether yielded purple lustrous crystals. Mass spectrometry: $C_{30}H_{46}N_3OS$ requires m/z=480; found m/z=480 ($I^-$ not detected by mass spectrometry).

Compound 28 3-(N,N-diethanolamino)-7-(N,N-dipentylamino)-phenothiazin-5-ium iodide (23%)

This compound was obtained following isolation of 3-(N,N-dipentylamino)-phenothiazin-5-ium triiodide and subsequent treatment with diethanolamine. Precipitation from dichloromethane by addition of diethyl ether yielded purple lustrous crystals. Mass spectrometry: $C_{26}H_{38}N_3O_2S$ requires m/z=456; found m/z=456 ($I^-$ not detected by mass spectrometry).

Further compounds have been synthesised and these are summarised in Table A. Compounds 5 and 6 are not compounds of the present invention and are included for comparative purposes.

Stock solutions of photosensitisers were made up in water and/or DMSO and stored in the dark until required. Test solutions were made up in buffer or solvent or biological medium as required.

Spectral and Physical Properties of the Phenothiazinium Compounds

Spectral data of the phenothiazinium compounds in water and in methanol (Table 1), show that all of the compounds have absorption peaks in the 650-700 nm region, but that there is considerable variability in the precise peak position.

The phenothiazinium compounds with longer alkyl chains have absorption peaks at longer wavelengths and the peak positions in general are at longer wavelengths in water compared with methanol. These differences probably reflect the aggregation state of the photosensitisers.

The octanol-water partition coefficients (p) for the various photosensitisers are shown in Tables 3 and 4, where p=log (mg/ml in octanol)/(mg/ml in buffer).

The octanol buffer partition coefficient (p) determines the lipophilicity of the drug. As might be expected, the lipophilicity increases with increasing value of R, but it should be noted that even for higher values of R, the compounds remain soluble in biological media.

TABLE 1

| | $R^1$ | $R^2$ | $R^3$ | $R^4$ | λmax in methanol (nm) |
|---|---|---|---|---|---|
| 1 | n-Pr | n-Pr | n-Pr | n-Pr | 656 |
| 2 | n-Bu | n-Bu | n-Bu | n-Bu | 661 |
| 3 | n-Pent | n-Pent | n-Pent | n-Pent | 665 |
| 4 | n-Hex | n-Hex | n-Hex | n-Hex | 668 |
| 5 | n-Me | n-Me | n-Me | n-Me | 669 |
| 6 | n-Et | n-Et | n-Et | n-Et | 669 |
| 7 | i-Bu | i-Bu | i-Bu | i-Bu | 668 |
| 8 | i-Pent | i-Pent | i-Pent | i-Pent | 662 |
| 9 | Me | Me | n-Pr | n-Pr | 659 |
| 10 | Et | Et | n-Pr | n-Pr | 661 |
| 11 | n-Bu | n-Bu | n-Pr | n-Pr | 665 |
| 12 | n-Pent | n-Pent | n-Pr | n-Pr | 665 |
| 13 | n-Hex | n-Hex | n-Pr | n-Pr | 666 |
| 14 | n-Bu | n-Bu | n-Pent | n-Pent | 660 |
| 15 | n-Bu | n-Bu | i-Pent | i-Pent | 661 |
| 16 | Et | Et | n-Hept | n-Hept | 661 |
| 17 | Me | n-Oct | Me | n-Oct | 655 |
| 18 | Et | Cyclohex | Et | Cyclohex | 668 |
| 19 | piperidino | | piperidino | | 667 |
| 20 | 2-ethylpiperidino | | n-Pent | n-Pent | 668 |
| 21 | 2-methyl pyrrolidino | | n-Pent | n-Pent | 663 |
| 22 | Morpholino | | Morpholino | | 660 |
| 23 | Morpholino | | n-Pr | n-Pr | 663 |
| 24 | Morpholino | | n-Bu | n-Bu | 661 |
| 25 | Morpholino | | n-Pent | n-Pent | 663 |
| 26 | $HO(CH_2)_2$ | $HO(CH_2)_2$ | n-Pr | n-Pr | 663 |
| 27 | $HO(CH_2)_2$ | $HO(CH_2)_2$ | n-Bu | n-Bu | 660 |
| 28 | $HO(CH_2)_2$ | $HO(CH_2)_2$ | n-Pent | n-Pent | 663 |
| 29 | $PhCH_2$ | $PhCH_2$ | $PhCH_2$ | $PhCH_2$ | 649 |

Ex. Max is the fluorescence excitation wavelength maximum and Em. Max is the fluorescence emission wavelength maximum Me, Et, Pr, Bu, Pent, Hex, Hept, Oct in the above table and throughout this specification represent methyl, ethyl, propyl, butyl, pentyl, hexyl, heptyl and octyl respectively, and that n- and i- indicate normal and iso alkyl chains.

The phenothiazinium derivatives were assessed for PDT efficacy in a series of mammalian cells in culture. RIF-1 murine fibrosarcoma cells were studied, using the MTT assay to assess remaining cell viability following PDT. The data from a series of experiments are summarised in Table 2 in which R in the Table represents $R^1$ and $R^2$, which shows the $LD_{50}$ values (concentration of photosensitiser needed to kill half of the cells under the conditions used) for four of the phenothiazine derivatives. Also shown for comparison are the data for methylene blue and ethylene blue. Some of these compounds are also able to kill cells in the dark and Table 2 also shows the ratio to $LD_{50}$ for dark only controls. It may be seen from Table 2 that the tetra-n-pentyl derivative, the tetra-n-butyl derivative and the tetra-n-propyl derivative are all efficient PDT agents under these conditions, being much more active than methylene blue or ethylene blue. The most efficient is the tetra-n-propyl derivative. Also, it is clear that, while for methylene blue there is only a small ratio between the $LD_{50}$ for dark and light toxicity, this ratio is much greater for the phenothiazinium derivatives. The results illustrate the much increased photoactivity of these compounds, but also their relative lack of dark toxicity compared with methylene blue. This is a considerable advantage in therapeutic terms. Table 2 also shows the relative activity of the various derivatives in comparison with methylene blue and ethylene blue using a measure of their intrinsic ability to produce singlet oxygen. It may be seen that there is very little difference between the different compounds, showing that the marked differences observed in cells is almost entirely due to biological factors, the mechanisms of which are not yet known. Table 2 also shows the initial subcellular localisation of the different phenothiazinium compounds derivatives compared with that of methylene blue and ethylene blue, as well as any re-localisation which occurs following light administration. It is noteworthy that, whilst all of the derivatives initially localise in lysosomes, whilst methyene blue then relocalises to the nucleus (with possible deleterious or mutagenic effects on DNA), the tetra-n-propyl, tetra-n-butyl, tetra-n-pentyl and tetra-n-hexyl derivatives relocalise to the mitochondria, which is a much better PDT target.

Table 3 shows $LD_{50}$ values for some of the derivatives in a series of different cells in culture, representing different human tissues and cancers. It is clear that the tetra-n-propyl, the tetra-n-butyl and the tetra-n-pentyl derivatives are again highly active compared with methylene blue and that they are also active in all cell lines tested.

Several asymmetric phenothiazinium derivatives (where $R^1=R^2 \neq R^3=R^4$) have been prepared and tested in cells in culture. Several of these have been tested and shown to have superior properties as photosensitisers to methylene blue, both in terms of absolute activity and in terms of the light to dark toxicity ratio. Sample data for these compounds are shown in Table 4.

TABLE 4

Chemical properties of the asymmetric phenothiazines in comparison to methylene blue and phototoxicity and dark toxicity in SiHa human cervical squamous cell carcinoma cells.

| | $λ_{max}$ in methanol (nm) | Singlet oxygen generation[1] | Log P | PDT $LD_{50}$ (μM)[2] | Ratio dark: PDT $LD_{50}$[2] |
|---|---|---|---|---|---|
| Methylene blue (compound 5) | 656 | 47 | −1.0 | 18.7 ± 1.0 | 1 |
| Di-n-butyl morpholino (compound 24) | 661 | 29 | +1.0 | 4.6 ± 2.0 | 7 |
| Di-n-butyl diethanolamine (compound 27) | 660 | 13 | +1.3 | 1.7 ± 0.3 | 87 |
| Di-n-pentyl diethanolamine (compound 28) | 663 | 32 | +1.1 | 0.43 ± 0.03 | 39 |

[1]% photo-oxidation of 1,3-diphenylisobenzofuran after 10 min red light illumination with 100 mg/ml of the phenothiazinium compounds in 90% DMF: 10% water.
[2]Cells were incubated with the phenothiazinium compounds for 2h. For measurement of phototoxicity, cells were illuminated with 3J/cm² 665 nm light. Dark toxicity was measured in parallel. Cell survival was assessed after 48 h using the sulforhodamine B (SRB) assay.

Anti-tumour Efficacy in Vivo

Tumour destruction was assessed in CBA/gy mice bearing subcutaneous CaNT tumours. Photosensitiser was administered intravenously at doses up to 16.7 μmol/kg. The dose was reduced to 8.35 μmol/kg if high levels of morbidity or mortality were observed or if solubility was limited. At various times after photosensitiser administration, the tumour was illuminated superficially with 60 J/cm2, 50 mW/cm2 light from a Paterson lamp using a 660±15 nm filter. Drug-light intervals ranged from 0 h (in practice, 1-2 minutes) up to 96 h. 72 h after illumination a cross sectional slice was removed from the centre of the tumour parallel to the incident light, an image of this was captured and the macroscopic necrotic area quantified using image analysis software. Necrosis was expressed as % area of the total tumour slice. % tumour necrosis in control tumours was generally <10%. Antitumour activity was categorized: None 0-10% tumour necrosis, Low 11-39% tumour necrosis, Medium 40-69% tumour necrosis, High 70-100% tumour necrosis.

Antitumour activity at the optimal dose and drug-light interval for each compound is shown in Table 5.

dependent on the nature of the alkyl groups, and the tetra-n-pentyl and tetra-n-butyl derivatives were particularly effective compared with methylene blue.

FIG. 2 shows the anti-tumour photodynamic efficacy (% tumour necrosis) for the tetra-n-propyl and tetra-n-pentyl derivatives as a function of the time interval between drug and light administration. These data show a quite unexpected difference between the two compounds. The tetra-n-propyl derivative is very active at very short drug-light time intervals (ie by giving light almost immediately after giving drug) whereas the tetra-n-pentyl derivative has very low activity at very short times, but much higher activity after 1 hour. The explanation for this finding is as yet unknown, but clearly these differential properties could be exploited for different applications. For example, the fast acting drug could be used for vascular treatments and the slower acting drug could be used for tumour cell treatments.

TABLE 5

PDT induced tumour necrosis in CBA/gy mice following iv administration at the optimal dose and drug - light interval, and Photoinactivation of log phase *E. coli* and *C. albicans* using 10 μM photosensitiser and illumination with 665 nm laser light, at a fluence rate of 3.2 J/cm$^2$, except for compounds 1, 4, 5, 6 which were illuminated at a fluence rate of 1.3 J/cm$^2$.

| | | Oncology | | | | | *C.albicans* Cell |
|---|---|---|---|---|---|---|---|
| Compound | Counter anion | Antitumour activity | % Tumour necrosis | Dose (μmol/kg) | Drug-light interval | Cell kill (Log$_{10}$ reduction in CFU/ml) | cell kill (Log$_{10}$ reduction in CFU/ml) |
| 5 | Cl$^-$ | None | 9 ± 4 | 16.7 | 1 h | 0.55 (0.02) | |
| 6 | I$^-$ | None | 2 ± 2 | 16.7 | 1 h | 0.23 (0.02) | |
| 1 | I$^-$ | High | 93 ± 3 | 16.7 | 0 h | 0.91 (0.12) | |
| 2 | Br$^-$ | High | 95 ± 3 | 8.35 | 0 h | 4.72 (0.30) | 4.16 (0.14) |
| 3 | Br$^-$ | High | 88 ± 6 | 1.67 | 1 h | 5.29 (0.25) | 3.61 (0.36) |
| 4 | Br$^-$ | Medium | 47 ± 12 | 8.35 | 0 h | | |
| | I$^-$ | | | | | 0.09 (0.02) | |
| 7 | Br$^-$ | High | 78 ± 3 | 16.7 | 0 h | 2.56 (0.09) | 4.15 (0.36) |
| 8 | Br | High | 74 ± 12 | 8.35 | 0 h | 3.58 (0.13) | |
| 9 | I$^-$ | Low | 34 ± 2 | 16.7 | 0 h | 2.82 (0.54) | |
| 10 | I$^-$ | Medium | 45 ± 15 | 16.7 | 0 h | 3.01 (0.14) | |
| 11 | I$^-$ | High | 98 ± 2 | 16.7 | 0 h | 4.86 (0.30) | |
| 12 | I$^-$ | Low | 38 ± 14 | 8.35 | 0 h | 4.50 (0.28) | 3.58 (0.97) |
| 13 | I$^-$ | High | 85 ± 3 | 8.35 | 0 h | 4.62 (0.34) | |
| 14 | I$^-$ | Medium | 60 ± 13 | 16.7 | 1 h | 3.25 (0.58) | |
| 15 | I$^-$ | High | 95 ± 3 | 16.7 | 0 h | 2.84 (0.30) | 5.81 (1.18) |
| 16 | I$^-$ | Low | 25 ± 13 | 16.7 | 1 h | 0.82 (0.01) | |
| 17 | Br$^-$ | Medium | 61 ± 11 | 16.7 | 0 h | 0.23 (0.14) | |
| 18 | Br$^-$ | Medium | 49 ± 14 | 16.7 | 0 h | 4.74 (0.10) | 2.41 (0.01) |
| 19 | I$^-$ | Low | 36 ± 10 | 16.7 | 0 h | 1.77 (0.03) | |
| 20 | I$^-$ | High | 86 ± 2 | 16.7 | 0 h | 3.56 (0.27) | 4.25 |
| 21 | I$^-$ | High | 90 ± 4 | 8.35 | 0 h | 3.21 (0.07) | |
| 22 | I$^-$ | Low | 17 ± 6 | 16.7 | 0 h | — | |
| 23 | I$^-$ | Low | 14 ± 7 | 16.7 | 0 h | 1.72 (0.30) | |
| 24 | I$^-$ | None | 10 ± 7 | 16.7 | 1 h | 1.90 (0.36) | |
| 25 | I$^-$ | Low | 16 ± 5 | 16.7 | 1 h | 1.70 (0.28) | |
| 26 | I$^-$ | Low | 17 ± 10 | 16.7 | 0 h | — | |
| 27 | I$^-$ | None | 3 ± 2 | 16.7 | 0 h | 0.8 | |
| 28 | I$^-$ | High | 75 ± 4 | 8.35 | 0 h | 1.5 | |
| 29 | I$^-$ | Medium | 40 ± 17 | 16.7 | 1 h | 1.54 (0.02) | |

FIG. 1 shows the anti-tumour photodynamic efficacy (% tumour necrosis) of symmetrically substituted phenothiazines of type (I). Female CBA/Gy mice with CaNT subcutaneous tumours were injected with a solution of the drug at a dose of 16.7 μmol per kilogram. They were treated with the optimum wavelength of light (determined in separated experiments) 1 hour after injection. The light source was a Paterson lamp with appropriate filters giving a bandwidth of 30 nm, and treatment was 60 J cm$^{-2}$ at a rate of 50 mW cm$^{-2}$. It can be seen from FIG. 1 that tumour response is very The present compounds have a number of advantages over currently available compounds such as Photofrin (trade mark, Axcan Pharma PDT Inc) and Foscan (trade mark, Bioscience Technology Investment Holdings Limited). For example the compounds of the present invention are single isomer free compounds produced by relatively simple processes, whereas Photofrin is a complex mixture of porphyrin derivatives. A short drug administration to light interval is desirable both in terms of patient convenience and time in hospital during treatment and associated costs. Photofrin requires a long drug administration to light interval, typically of 48 hours, otherwise unacceptable damage to normal tissues surrounding the tumour occurs at short drug-to-light intervals. The compounds of the present invention, for example the tetra-n-pentyl derivative provides a high level of tumour necrosis (70%) where illumination is immediately after administration and 90% where illumination is 1 hour after administration. To achieve comparable levels of necrosis a 5-fold higher dose of Photofrin was required, Comparison of damage to skin (assessed by scab formation) shows that with the present compounds, for example the tetra-n-pentyl derivative, no scab formation is observed at any drug to light interval whereas Photofrin gave up to 25% scab formation at short drug to light intervals (0-3 hours), longer drug to light intervals of 48 hours gave no scab formation but tumour necrosis was only 50%.

For another available compound, Foscan, there is a delay of 4 days, to allow time for accumulation in the cancer cells, between injection into the bloodstream and activation with laser light. Administration of Foscan results in patients becoming highly sensitive to light, with a the period of sensitivity of approximately 15 days.

FIG. 3 shows the relative skin photosensitivity caused by the tetra-n-butyl and tetra-n-pentyl derivatives, compared with polyhaematoporphyrin, PHP (equivalent to Photofrin). Photofrin is the current leading PDT agent for oncology, but has the major disadvantage of causing prolonged skin photosensitivity in patients. In this model, the skin photosensitivity is measured in terms of the increase in ear thickness 24 hours after exposure to drug and light. FIG. 3 shows that, as expected, PHP shows a high level of skin photosensitivity, but the two phenothiazinium derivatives show little or no skin photosensitivity. These two derivatives also caused very little skin colouration based on administration of the tetra-n-pentyl derivative to CBA/gy mice. The difference in skin coloration between pre- and post-drug administration at dose rates of 16.7 μmol/kg, i.e 10 fold higher than necessary to achieve 90% tumour necrosis, does not induce any skin coloration. Coloration was comparable to control animals injected with saline.

Photo-antimicrobial Activity

1) General Methods

Method for Microbial Bacterial Photoinactivation Experiment a) Standard Preparation of Photosensitsiers Stock solutions of the photosensitisers were made up to 5 mM in dimethylsulfoxide (DMSO). The 5 mM stock was further diluted in DMSO to a working concentration of 1 mM. All photosensitisers were stored in foil covered vials at room temperature until required.

b) Standard Preparation of Microorganisms

The standard protocol outlined below was modified as appropriate to study variation of various experimental parameters.

A single bacterial colony from an agar plate was used to aseptically inoculate 100 ml of nutrient media (0.5% yeast extract: 1.0% tryptone w/v) in a 1 l conical flask. For *C. albicans* a single fungal colony was used to inoculate 100 ml of sabouraud dextrose media in a 1 l conical flask. The culture was incubated in a shaking incubator overnight, at 37° C. The incubator was set to 250 strokes per minute and a rotary motion of a 2.5 cm circle. This culture was used for the stationary phase experiments. For the log phase bacterial experiments the overnight culture was used to inoculate 200 ml of nutrient media (in a 2 l bevelled flask), for *C. albicans* 200 ml of sabouraud dextrose media was inoculated, both were to an optical density of 0.1 at 600 nm. The microorganisms were grown until in the mid-logarithmic phase and then harvested and resuspended.

c) Preparation of Microorganisms for PDT

The log or stationary phase cells were collected by centrifugation and washed twice in 0.1 M potassium phosphate buffer (pH 7.0). Following washing, the cells were resuspended in the same buffer to an absorbance of 0.87 at 650 nm. This absorbance was equivalent to $3.5 \times 10^8$ CFU/ml or 8.5 $\log_{10}$CFU/ml for *E. coli, S. aureus*, MRSA and *P. aeruginosa*. For *C. albicans* this correlated to $1.0 \times 10^7$ CFU/ml or 7.0 $\log_{10}$CFU/ml. For photoinactivation of *E. coli* cells in media, the bacteria were resuspended in nutrient media at this stage.

Microbial Cell Photoinactivation Experiments

Standard Incubation with Photosensitiser 25 ml of the prepared cell suspension was incubated with 0.25 mls of a 1 mM stock solution of photosensitiser (giving a final concentration of 10 μM) in a 250 ml sterile foil covered conical flask. The suspension was incubated for 30 minutes in the dark in a 37° C. shaking incubator at 250 rpm.

Illumination from a White Light Source

After incubation with 10 μM phenothiazinium compound, the suspension was irradiated by a 500 W halogen lamp, from a distance of 75 cm, for 60 minutes, the power of the lamp was 1.3 mW/cm² giving 4.68 J/cm² over the hour illumination.

Illumination from a 665 nm Laser

After incubation with 10 μM phenothiazinium compound, 10 ml of the bacterial culture was aseptically transferred to a sterile cell. This consisted of a sealed vial with a sealed capillary tube inserted, into which the optical fibre could be placed. Illumination was carried out with a Ceram Optec diode laser (665 nm) which used an optical fibre with a 3 cm diffusing tip, at 100 mW. For experiments comparing the phenothiazinium compound series in *E. coli*, samples were illuminated for 4 min. This equated to a fluence rate of 5.3 mW/cm² assuming that the area of the illuminated cylinder was 18.86 cm². After a 4 min illumination the total fluence was 1.3 J/cm². Other experiments used a 10 min illumination and 50 μl samples were removed for CFU analysis after 0, 1, 2, 4, 8 and 10 min illumination. These illumination times are equivalent to the following fluences respectively: 0 J/cm²; 0.32 J/cm²; 0.64 J/cm²; 1.3 J/cm²; 2.5 J/cm² or 3.2 J/cm². Oxygen electrode traces showed oxygen was not limiting during the illumination period. For experiments comparing the effect of tetra-n-pentyl-3,7-diaminophenothiazin-5-ium compound on different bacteria illumination used the laser set up but for 10 minutes giving a light dose of 3.2 J/cm². This light dose was also used for experiments comparing compounds 17-29. Results are tabulated above in Table 5 and below in Table 6.

Bacterial and Yeast Survival Analysis 50 ml of the illuminated and non-illuminated samples of the suspension were removed and diluted in 0.1 M pH 7.0 potassium phosphate buffer. 50 μl of the diluted suspension was then plated on nutrient agar (0.5% yeast extract, 1.0% tryptone, 2.0% agar w/v) for bacteria, or sabouraud dextrose agar for *C. albicans*. The plates were incubated overnight at 37° C. to give a number of colony forming units between 30-300. Cell inactivation was then measured.

Control studies involving plating out of bacteria before and after the 30 minute incubation step with no phenothiazinium compound but 0.25 mls DMSO showed no change in CFU/ml. Illumination of the bacterial culture alone with no phenothiazinium compound but 0.25 mls DMSO also demonstrated no change in CFU. For illumination in nutrient media, control tests showed a $\log_{10}$ increase in CFU/ml of 0.2 during the hour illumination.

Determination of the Effect of Phenothiazinium Compounds on Bacterial Cell Growth 200 ml of nutrient media (0.5% yeast extract 1.0% tryptone w/v) in foil covered 250 ml conical flasks was aseptically innoculated with 10 ml of a fully grown bacterial culture (*E. coli*). In addition the media contained 1.0 ml of a 1 mM stock solution of phenothiazinium compounds with a final concentration of 10 µM, apart from the control which contained no phenothiazinium compounds but 1.0 ml DMSO.

The suspension was incubated at 37 C and 250 rpm in a shaking incubator in the dark. 1 ml samples were taken every hour for 6 hours and turbidity based on apparent optical density at 550 nm caused by light scattering was measured. Control studies show this wavelength is out of the region of photosensitiser absorption. Following optical density readings the 1.0 ml sample was spun in a MSE Micro-Centaur centrifuge (10 000 g×5 minutes) and the absorbance spectra of the supernatant read spectrophotometrically.

For the tetra-n-butyl derivative only, similar experiments were carried out where the bacteria were allowed to grow without photosensitiser for 3 hours, after which time the phenothiazinium compounds was added. Subsequent growth was monitored as a function of time, both for exposure to light and in the dark.

Uptake of the Photosensitisers into *E. coli*

Following incubation of the bacteria with photosensitiser, 2 ml of the non-illuminated bacterial culture was sedimented using a Benchtop Centaur 5 centrifuge (1500 g×10 min). The bacterial pellet was washed twice with 0.1 M potassium phosphate buffer (pH 7.0) to remove extracellular and loosely bound photosensitiser.

Finally the pellet was resuspended and vortexed in 1 ml of 0.1 M NaOH 2% (w/v) SDS and left at room temperature, in the dark, for at least 24 h. Fluorescence readings were taken using a Kontron SFM-25 spectrofluorimeter. The concentration of phenothiazinium compound in the cellular samples was determined from interpolation of the standard curves.

Photobleaching 0.25 mls of a 1 mM solution of photosensitiser, 0.25 mls of 10 mM tryptophan was added to 25 mls of 60% methanol, 40% potassium phosphate buffer (pH7.0). Experiments were also carried out in the absence of tryptophan where this was replaced by 0.25 mls of the 60% methanol, 40% potassium phosphate buffer (pH7.0).

The mixture was illuminated as in the cell inactivation experiments above (1.3 mW/cm$^2$) for 60 minutes, samples were taken every 15 minutes and spectra recorded on a UV-Visible spectrophotometer between 500 nm and 700 nm. For high light dose, illumination was at 9 mW/cm$^2$ for 60 minutes.

Results

Antibacterial Properties of Phenothiazinium Derivatives

FIG. 4 shows log change in Colony Forming Units (CFU)/ml of *E.coli* incubated for 30 minutes with 10 µM phenothiazinium compound and illuminated for 60 minutes at 1.3 mW/cm$^2$. Data were recorded of cell survival following a 60 minute illumination by a halogen lamp. It may be seen that there is substantial bacterial inactivation with the trend in the group being a decrease from methylene blue to ethylene blue, followed by an increase of almost 1000 fold up to the tetra-n-butyl phenothiazinium derivative. The longer chain phenothiazinium compounds then show reduced bacterial cell kill ability such that the tetra-n-hexyl derivative is almost inactive. The tetra-n-butyl phenothiazine led to the largest change in colony forming units per ml of 5.1 $\log_{10}$ equivalent to a percentage cell survival of 0.001%. The lowest change of 0.19 $\log_{10}$ CFU was using the tetra-n-hexyl derivative which is a cell survival of 65.3%. There was no cell inactivation with a light only control.

FIG. 5 shows the log change in CFU/ml of *E.coli* incubated for 30 minutes with different concentrations of tetra-n-butyl phenothiazinium derivative and illuminated for 15 minutes at 1.3 mW/cm$^{-2}$. 10 µM was the most effective concentration tested for bacterial inactivation using tetra-n-butyl phenothiazinium derivative. The log change in CFU/ml with this concentration was 4.59 $\log_{10}$ units. Cell kill effects were achieved with all of the concentrations tested but were reduced at the lower drug doses. At 50 µM there is a log change of 2.15 units which is reduced compared to 10 µM. This could be due to photosensitiser aggregation and therefore lower drug doses to the cell.

Many antibiotics are only poorly effective against non-growing or stationary bacteria and it is important to assess the ability of the phenothiazinium compounds to inactivate stationary phase bacteria. During the stationary period the cell has a thicker peptidoglyan cell wall and differences in protein metabolism and therefore might be less susceptable to the photodynamic effect. FIG. 6 shows the log change in CFU/ml of *E.coli* in the stationary phase of growth following incubation for 30 minutes with 10 µM phenothiazinium compounds and illuminated for 60 minutes at 1.3 mW/cm$^2$. It may be seen that the effectiveness of the tetra-n-propyl and tetra-n-butyl derivatives is only slightly reduced against stationary phase bacteria, with again the tetra-n-butyl derivative being the most effective.

Inactivation of bacteria may be more challenging in a therapeutic environment, because the sensitiser may bind preferentially to extracellular proteins rather than the bacterial lipopolysaccharide membrane. This was tested by resuspending the bacteria in nutrient medium containing many factors which might compete with bacterial cells for photosensitiser binding. FIG. 7 shows the log change in CFU/ml of *E.coli* resuspended in nutrient medium, from which it may be seen that there is little reduction in the level of cell kill. Again, the tetra-n-butyl phenothiazinium derivative has the highest antibacterial activity.

FIG. 8 shows the log change in CFU/ml of *E. coli* following incubation with 10 µM phenothiazinium compound for 30 minutes and illumination with laser light (665 nm) for only 4 minutes at 0.1 W. Again, the same pattern of activity among the phenothiazine derivatives is seen, showing that the effects are present with coherent laser light. The potential advantages of a laser source are increased accuracy of light doses and shorter illumination times.

Further studies with laser light showed that a log change of 5.69 CFU/ml can be achieved with a 14 minute illumination at 0.1 W with the tetra-n-butyl phenothiazinium derivative and that after a 20 minute illumination there is a log change of almost 8.5 units, though the number of CFU are too small to make this figure statistically reliable Uptake of the photosensitisers into bacterial cells is clearly important in determining photo-activity. FIG. 9 shows uptake of 10 µM phenothiazinium compounds into *E. coli* cells following a 30 minute incubation. Cells were washed twice in 0.1M pH7.0 potassium phosphate buffer to remove extra-cellular or loosely bound sensitiser. It may be seen that uptake of the phenothiazinium compounds is somewhat correlated with phototoxicity in that the tetra-n-butyl derivative is taken up the most by the bacterial cells.

However, the correlation between uptake and photoactivity is far from exact. For example, the ratio between the photoactivity and the uptake for the tetra-n-butyl derivative is far greater than that for the tetra-n-hexyl derivative. These ratios would be expected to be the same for all of the derivatives if the photoactivity could be explained only on the basis of uptake. It is therefore clear that the extremely high activities of the tetra-n-butyl and tetra-n-propyl derivatives must be due to some additional factors, as yet unknown.

Data not shown have proved that the tetra-n-butyl derivative is taken up very quickly into the *E.coli*; there are no differences in uptake between incubation times of 5 minutes and 30 minutes. However, in the presence of nutrient medium, the uptake was found to be somewhat slower and reduced in extent.

FIG. 10 shows the log change in CFU/ml of *E. coli* cells incubated with 10 µM tetra-n-butyl phenothiazinium derivative and then washed twice with 0.1M pH7 potassium phosphate buffer to remove any extra-cellular or loosely bound photosensitiser, which may have an effect on the phototoxicity. Illumination used laser light (665 nm) at 0.1 W for 4 minutes. The results show there is little difference between the log change in CFU/ml of washed and unwashed cells, indicating that it is the tightly bound photosensitiser which is causing cell death. At present, the precise location of the photosensitiser within the bacterial cell is not known but the photodynamic action is effective and non-recovering.

Data for the effect of the different phenothiazinium compounds on the growth of an *E. coli* culture in the dark as compared to a control are shown in FIG. 11. Incubation was carried out in the dark at 37° C. for 6 hours and measurements were based on apparent turbidity at 550 nm as described earlier. All the cultures containing phenothiazinium compounds show reduced growth as compared to the control with the tetra-n-butyl phenothiazinium derivative showing the greatest inhibition in the number of cells in the bacterial suspension. It should be emphasised that this dark inhibition is many orders of magnitude less than that observed for cell inactivation in the light.

Further work was carried out with the tetra-n-butyl derivative alone to determine the effect of photosensitiser plus light on growth of bacteria. These data, shown in FIG. 12 show clearly that for the growing bacteria with addition of photosensitiser after 3 hours, there is continuing growth in the dark, but complete elimination of growth in the light. The data again illustrate the very powerful photobacteriocidal effect of this photosensitiser.

FIG. 13 shows percentage cell survival of *Pseudomonas aeruginosa* following incubation with 10 µM tetra-n-butyl phenothiazinium derivative. Illumination was with laser light (665 nm) at 0.1 W. *P aeruginosa* is a Gram negative organism which is commonly associated with a number of skin conditions including infections of ulcers and burn wounds. The figure shows that the tetra-n-butyl phenothiazinium derivative can photodynamically inactive this organism extremely efficiently. An illumination time of only 2 minutes with laser light (665 nm) at 0.1 W leads to a greater than 99% cell kill, while increase of the illumination time to 10 minutes gives almost 4 logs of cell kill. Control studies showed that there is no reduction in cell number caused by the illumination alone in the absence of photosensitiser with 10 µM tetra-n-butyl phenothiazinium derivative.

FIG. 14 shows percentage cell survival of *Staphylococcus aureus* following incubation with 10 µM tetra-n-butyl phenothiazinium. Illumination was with laser light (665 nm) at 0.1 W. *S. aureus* is a Gram positive organism which differs from Gram negative organisms in that it has a thick outer peptidoglycan layer and no external lipopolysaccharide. The bacterial structure is the same as in MRSA (Methicillin resistant *S. aureus*) which is resistant to almost all commonly used antibiotics. The data show that after only a 1 minute illumination almost 99% of the bacteria are inactivated and that after 10 minutes there is almost 5 logs of cell kill, illustrating the very high photoactivity of the tetra-n-butyl derivative against this Gram positive organism.

It is important to determine if the photosensitiser would also be active against the antibiotic resistant form, MRSA, as this would have major health and industrial applications. FIG. 15 shows percentage cell survival of MRSA following illumination with 665 nm laser light at 0.1 W and incubation with 10 µM tetra-n-butyl phenothiazinium derivative. The data clearly show that this photosensitiser is indeed highly photoactive in killing MRSA.

Anti-fungal Properties of Phenothiazinium Derivatives

In order to test the ability of the tetrabutyl derivative to kill fungal cells in the light, the photosensitiser was incubated with cells of *Candida albicans* and the culture was subjected to laser light as described above. The results are shown in FIG. 16, in which it is clear that this eukaryotic organism is also readily destroyed. This photosensitiser is therefore also highly photoactive against this fungal organism which is responsible for many common infections e.g. thrush.

Selectivity for Bacterial Cells Versus Mammalian Tissues

It is clearly important for therapeutic purposes that there is minimal damage to host tissues while microorganisms are being destroyed. This was tested by applying a solution of the tetra-n-butyl phenothiazinium derivative to the ears of experimental mice and illuminating, under conditions in which the total dose was almost 20 times that needed for bacterial or fungal elimination. The possible effects on the host tissue were assessed by measuring any increase in ear thickness. This is a standard model for detecting photodynamic reactions in the skin. FIG. 17 shows the data obtained, compared with results from intravenous administration of PHP, a drug equivalent to Photofrin which is known to cause prolonged skin reaction. It is clear from FIG. 17 that, while the reaction from PHP is very strong, as expected, there is little or no reaction from the tetra-n-butyl phenothiazinium derivative, suggesting that mammalian tissues would not be damaged during antimicrobial treatment.

Photobleaching

Photobleaching removes detectable colour from the photosensitiser, rendering it inactive and is the result of its instability to light and reduction or oxidation. Such photobleaching may have advantages or disadvantages depending on the potential application. For example, photobleaching is undesirable in the coating of lines and catheters. Two sets of experiments were carried out; one at a high light dose (9.0 mW/cm$^2$) and one at a low light dose (1.3 mW/cm$^2$) with and without tryptophan as described above. Absorption spectra at low light dose, with and without tryptophan, showed no changes for any of the phenothiazinium compounds demonstrating they are stable at this dose. At the high light dose, spectral changes were observed for the methylene blue, indicating photobleaching. The maximum absorbance decreased and the wavelength peak shifted over the one hour illumination. These changes occurred to the same extent with and without tryptophan. However, none of the other phenothiazinium compounds showed this degradation and remained stable to photobleaching at the high light dose.

The antibacterial properties of tetra-n-pentyl-3,7-diaminophenothiazin-5-ium are tabulated below:

TABLE 6

Photoinactivation of bacteria and yeast in the log and stationary growth phase, following incubation with 10 μM photosensitiser and illumination with 665 nm laser light at a fluence rate of 3.2 J/cm².

| Photosensitiser | Bacteria/Yeast | Growth phase | Cell kill (log reduction in CFU/ml) | Standard error of the mean |
|---|---|---|---|---|
| Tetra-n-pentyl-3,7-diaminophenothiazin-5-ium | P. aeruginosa | Log | 3.88 | 0.27 |
| | | Stationary | 1.28 | 0.22 |
| | S. aureus | Log | 4.21 | 0.22 |
| | | Stationary | 3.17 | 0.04 |
| | MRSA | Log | 3.80 | 0.34 |
| | | Stationary | 1.85 | 0.16 |
| | C. albicans | Log | 3.61 | 0.36 |

The data in the table above show the log reduction in CFU/ml of bacteria or yeast incubated with 10 μM photosensitiser, and illuminated using a 665 nm laser for 10 min, at a fluence of 3.2 J/cm².

The susceptibility of bacteria to phenothiazinium mediated PDT can depend on if the bacteria are Gram-positive or Gram-negative. Gram-positive bacteria (S. aureus, MRSA) have a highly cross linked peptidoglycan cell wall approximately 25 nm in thickness. Gram negative bacteria (E. coli, P. aeruginosa) have a thinner 5 nm cell wall and a unique lipopolysaccharide outer membrane. The presence of the outer membrane gives an increased resistance of Gram negative bacteria to many antibacterial agents.

Following illumination the tetra-n-pentyl-3,7-diaminophenothiazin-5-ium compound led to >3 log reduction in CFU/ml for both log phase, Gram negative (E. coli, P. aeruginosa) and Gram positive bacteria (S. aureus, MRSA).

Many antibiotics have a low activity against bacteria in the stationary growth phase. Bacteria in the two growth phases differ in their physiology and morphology. Stationary phase cells are less active and more resistant to environmental stress, therefore, may be resistant to phenothiazinium mediated PDT. The above table shows that the effectiveness of the tetra-n-pentyl-3,7-diaminophenothiazin-5-ium compound is only slightly reduced against stationary phase cells compared to log phase cells.

MRSA, an antibiotic resistant strain of S. aureus is a major cause of nosocomal infection. MRSA and S. aureus are equally susceptible to tetra-n-pentyl-3,7-diaminophenothiazin-5-ium compound mediated anti microbial PDT. There was a log reduction of 3.80 $\log_{10}$CFU/ml using the tetra-n-pentyl-3,7-diaminophenothiazin-5-ium compound against log phase MRSA.

Phenothiazinium Compounds of Formula I Suitable for Inclusion in Polymers or Attachment to, or Adsorption on, Polymer Surfaces (a) Inclusion within Polymers

EXAMPLE

To a clear solution of cellulose triacetate (0.5 g) in dichloromethane (10 cm³) was added sensitiser (Formula 1 in which A=B=NR¹R² and R¹=R²=n-Bu) (0.01 g) and the mixture was stirred until the sensitiser had dissolved completely. The solution was then cast on a glass plate and allowed to dry slowly, giving a clear blue film. The film showed typical singlet oxygen generating properties on exposure to light. Thus an aerated red solution of tetraphenylcyclopentadienone (a characteristic singlet oxygen detector) in toluene containing the film was rapidly bleached on exposure to light from a 40 w tungsten filament lamp. An identical solution showed no bleaching when irradiated for the same period of time in the absence of the film.

(b) Adsorption on Polymers

Phenothiazinium compounds Ia and Ib were made according to the following reaction scheme and were isolated as dark blue solids. They were characterised by mass spectrometry.

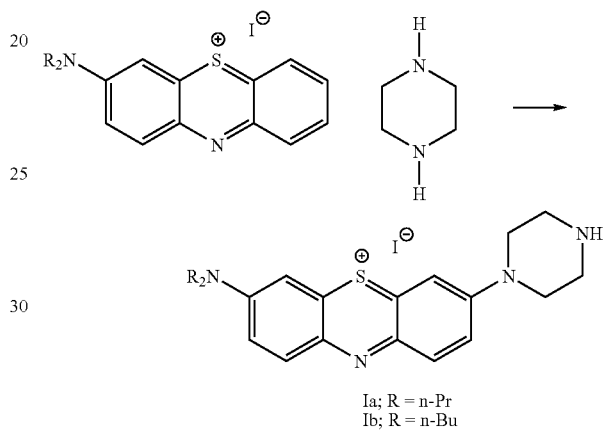

Ia; R = n-Pr
Ib; R = n-Bu

Compounds (Ia and Ib) were extremely basic and readily protonated in dilute acids to give (IIa) and (IIb) respectively, which could be adsorbed strongly on polymeric surfaces, e.g. polyamides, polyacrylates, polyesters, polycarbonates, polyurethanes, and strongly resisted removal by water or solvents. Alternatively Ia or Ib could be adsorbed directly onto acidic surfaces to give their corresponding cationic salts directly.

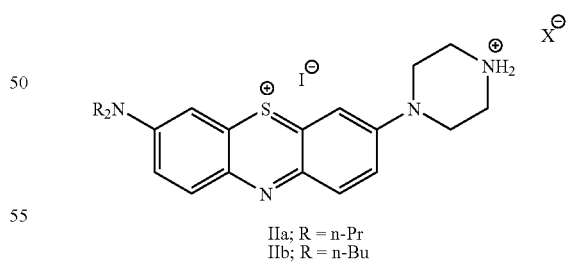

IIa; R = n-Pr
IIb; R = n-Bu (c) Covalent Attachment of the Phenothiazinium Sensitisers to Polymer Substrates Derivatives Ia and Ib Compounds Ia and Ib proved very reactive as nucleophiles in various substitution reactions that could provide a means of attaching the sensitiser unit covalently to polymers.

Thus reaction with anhydrides occurred, as exemplified by the following reaction:

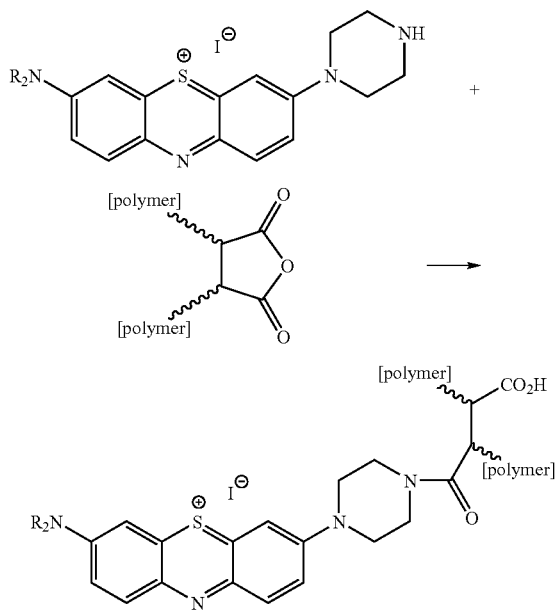

EXAMPLE

Polyethylene-graft-maleic anhydride (1.0 g) was dissolved in toluene (25 cm$^3$) with warming. The sensitiser Ia (0.20 g) was added and reaction mixture heated under reflux for 1 hour. The mixture was poured into methanol and the precipitate was filtered off, washed with methanol and dried, giving the sensitiser-bound copolymer as a dark blue powder (1.1 g). Covalent attachment of the sensitiser to the polymer was confirmed by dissolving the powder in dichloromethane and precipitating it by addition of methanol. No blue colour remained in the supernatant liquid.

A similar nucleophilic substitution reaction will occur with polymers containing ester

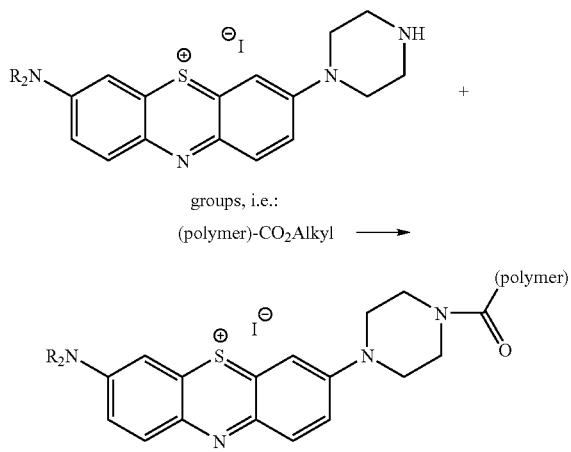

Phenothiazinium derivatives Ia and Ib are also very reactive towards chlorotriazine derivatives, and their linkage to polymers can be carried out by the following procedure:

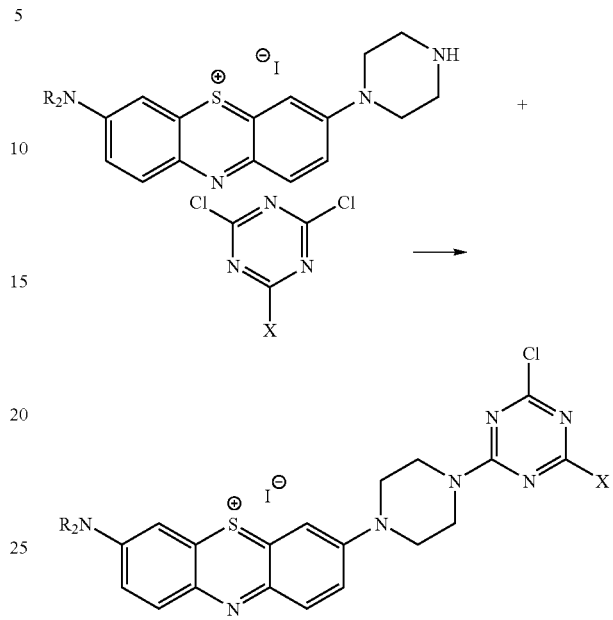

Where
  X=—NH-(Polymer) in the case of polyamide polymers
  X=—O-(Polymer) in the case of cellulosic polymers Alternatively, the residual chlorine in the previous example can be replaced by other reactive groups, as in the following reaction:

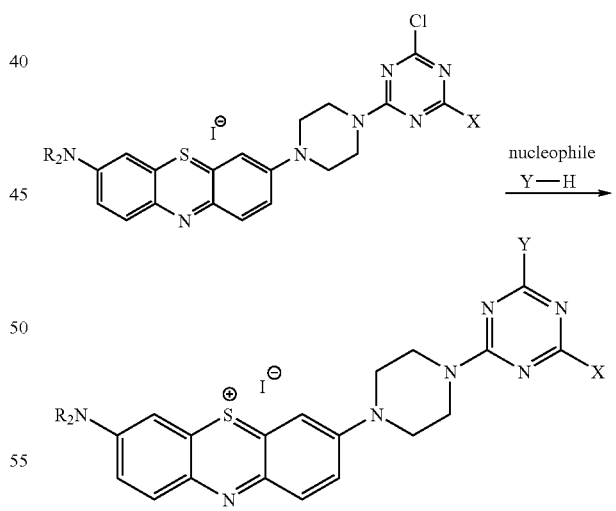

Where X and Y=—NH-(polymer)
Or X and Y=—O-(polymer)
Or X may be an amine —NHR or —NRR', and Y=—NH-(polymer), or —O-(polymer)

These are not the only means of attaching the phenothiazinium derivatives to polymers, and other methods may by employed based on existing polymer-grafting chemistry known to those skilled in the art.

EXAMPLE

Sodium carbonate (0.20 g) and cyanuric chloride (0.30 g) were added to a solution of the sensitiser Ia (0.26 g) in dry acetone (170 cm$^3$) at room temperature, and the mixture was stirred for 15 minutes. A sheet of transparent cellulose film (2.2 g) was immersed in an aqueous solution of sodium hydroxide (1M; 500 cm$^3$) for 10 minutes and then washed free of sodium hydroxide. This was then introduced into the sensitiser solution and the stirred mixture heated at 50° C. for 15 minutes. Water (200 ml) was added and the mixture heated at 60° C. for 30 minutes. The blue cellulose film was then removed and washed with water, and then heated in sodium carbonate solution (6%)to remove any unfixed dye. Covalent attachment to the cellulose was confirmed by heating the film in boiling sodium carbonate solution or boiling methanol, when no blue colour was removed. The film showed typical singlet oxygen generating properties on exposure to light, and when immersed in an air-saturated solution of tetraphenylcyclopentadienone in toluene and exposed to light from a 40 w tungsten filament lamp, the red dienone was bleached more rapidly than an identical solution containing no film.

REFERENCES

Wainwright M, Phoenix D A, Laycock S L, Wareing D R A, Wright P A. (1998). Photobactericidal activity of phenothiazinium dyes against methicillin-resistant strains of *Staphylococcus aureus*. FEMS Microbiology Letters 160, 177-181.

Wagner S J, Skripchenko A, Robinette D, Foley J W, Cincotta L (1998). Factors affecting virus photoinactivation by a series of phenothiazine dyes. Photochemistry and Photobiology 67, 343-349.

TABLE 3

Phototoxicity and dark toxicity of the phenothiazines in human tumor cell lines.

| R | OE33[1] | SiHa[2] | HT1376[3] | HT29[4] |
|---|---|---|---|---|
| Methyl | | | | |
| PDT LD$_{50}$ (μM) | 43.5 ± 1.8 | 18.7 ± 1.0 | 37.9 ± 10.1 | 88.5 ± 6.1 |
| Ratio dark:PDT LD$_{50}$ | 2.0 | 1.0 | 1.6 | 1.5 |
| Propyl | | | | |
| PDT LD$_{50}$ (μM) | 0.30 ± 0.09 | 0.075 ± 0.015 | 0.20 ± 0.13 | 0.22 ± 0.04 |
| Ratio dark:PDT LD$_{50}$ | 11 | 80 | 13 | 18 |
| Butyl | | | | |
| PDT LD$_{50}$ (μM) | | 0.28 ± 0.06 | | |
| Ratio dark:PDT LD$_{50}$ | | 18 | | |
| Pentyl | | | | |
| PDT LD$_{50}$ (μM) | | 0.29 ± 0.06 | 0.75 ± 0.22 | 1.49 ± 0.41 |
| Ratio dark:PDT LD$_{50}$ | | 11 | 6 | 4 |

[1] oesophageal adenocarcinoma
[2] cervical squamous cell carcinoma
[3] bladder transitional cell carcinoma
[4] colon adenocarcinoma Cells were incubated with the phenotiazine for 2 h. For measurement of phototoxicity, cells were illuminated with 3 J/cm$^2$ (10 mW/cm$^2$) 665 nm light. Dark toxicity was measured in parallel. Cell survival was assessed after 48 h using the sulforhodamine B (SRB) assay.

TABLE 2

Chemical properties of the phenothiazines and phototoxicity, dark toxicity, cellular uptake and subcellular localisation in RIF-1 murine fibrosarcoma cells.

| R | Singlet oxygen generation[1] | PDT LD$_{50}$ (μM)[2] | Ratio dark: PDT LD$_{50}$[2] | Uptake at PDT LD$_{50}$ (nmol/mg protein)[3] | Initial localisation[4] | Relocalisation + light[4] | LogP |
|---|---|---|---|---|---|---|---|
| Methyl | 47 | 54 | 3 | >4.6 | Lysosomes | Nucleus | −1.0 |
| Ethyl | 42 | 3.9 | 27 | 2.9 | Lysosomes | Lysosomes | +0.2 |
| Propyl | 40 | 0.42 | 19 | 0.9 | Lysosomes | Mitochondria | +1.1 |
| Butyl | 41 | 1.1 | 7 | 3.1 | Lysosomes | Mitochondria | +1.1 |
| Pentyl | 39 | 0.74 | 10 | 1.6 | Lysosomes | Mitochondria | +1.7 |
| Hexyl | 35 | 2.1 | 4 | 1.6 | Lysosomes | Mitochondria | +1.3 |

[1] % photo-oxidation of 1,3-diphenylisobenzofuran after 10 minutes red light illumination with 100 mg/ml of the phenothiazine in 90% DMF: 10% water.
[2] Cells were incubated with the phenothiazine for 2 h. For measurement of phototoxicity, cells were illuminated with 3 J/cm$^2$ (10 mW/cm$^2$) white light. Dark toxicity was measured in parallel. Cell survival was assessed after 24 h using the MTT assay.
[3] Cells were incubated with the phenothiazine for 2 h. Cells were solubilised in 2% SDS and the phenothiazine levels measured by fluorescence.
[4] Cells were incubated with the PDT LD$_{50}$ concentration of the phenothiazine for 2 h and fluorescence images captured before and during 10 min illumination with 630 nm light.

What is claimed is:

1. A method of treatment of a fungal infection due to *Candida albicans*, Gram negative bacterial infection due to *E. coli* or *P. aeruginosa*, or Gram positive bacterial infection due to *S. aureus* or methicillin resistant *S. aureus*, the method comprising administering to a subject having an area infected with *Candida albicans, E. coli, P. aeruginosa, S. aureus* or methicillin resistant *S. aureus*, by systemic administration or by local application to said infected area, a therapeutically effective amount of a compound selected from the group consisting of:

[3,7-(tetra-n-propylamino)-phenothiazin-5-ium]$_P$ X$^{P-}$,
[3,7-(tetra-n-butylamino)-phenothiazin-5-ium]$_P$ X$^{P-}$,
[3,7-(tetra-n-pentylamino)-phenothiazin-5-ium]$_P$ X$^{P-}$,
[3,7-(tetra-iso-pentylamino)-phenothiazin-5-ium]$_P$ X$^{P-}$,
[3-(N,N-di-n-butylamino)-7-(N,N-di-n-propylamino)-phenothiazin-5-ium]$_P$ X$^{P-}$,
[3-(N,N-di-n-hexylamino)-7-(N,N-di-n-propylamino)-phenothiazin-5-ium]$_P$ X$^{P-}$,
[3-(2-ethylpiperidino)-7-(N,N-di-n-pentylamino)-phenothiazin-5-ium]$_P$ X$^{P-}$,
[3-(2-methylpyrrolidino)-7-(N,N-di-n-pentylamino)-phenothiazin-5-ium]$_P$ X$^{P-}$,
[3,7-(N,N-tetra-iso-butylamino)-phenothiazin-5-ium]$_P$ X$^{P-}$,
[3-(N,N-di-n-butylamino)-7-(N,N-di-iso-pentylamino)-phenothiazin-5-ium]$_P$ X$^{P-}$,
[3-(N,N-diethylamino)-7-(N,N-di-n-propylamino)-phenothiazin-5-ium]$_P$ X$^{P-}$,
[3-(N,N-di-n-pentylamino)-7-(N,N-di-n-propylamino)-phenothiazin-5-ium]$_P$ X$^{P-}$,
[3-(N,N-di-n-butylamino)-7-(N,N-di-n-pentylamino)-phenothiazin-5-ium]$_P$ X$^{P-}$, and
[3-((N-ethyl-N-cyclohexyl) amino)-7((-N-ethyl)-N-cyclohexyl) amino-phenothiazin-5-ium]$_P$ X$^{P-}$, wherein X$^{P-}$ is a counteranion and P is 1, 2 or 3,
and exposing said infected area to light to render active said compound and
thereby effecting said treatment of said fungal infection, said Gram negative bacterial infection or said Gram positive bacterial infection.

2. The method according to claim 1 wherein said compound is [3,7-(tetra-n-butylamino)-phenothiazin-5-ium]$_P$ X$^{P-}$.

3. The method according to claim 1 wherein said method comprises administering to said subject, by local application to said infected area, said therapeutically effective amount of said compound of Formula (I).

4. The method according to claim 1 wherein said method is a method of treating said Gram negative bacterial infection or said Gram positive bacterial infection.

5. The method according to claim 4 wherein said method is a method of treating said Gram positive bacterial infection due to methicillin resistant *S. aureus*.

6. The method according to claim 1 wherein said fungal infection, Gram negative bacterial infection or Gram positive bacterial infection is present at a burn wound, ulcer or surgical wound.

7. The method according to claim 1 wherein said fungal infection, Gram negative bacterial infection or Gram positive bacterial infection is present on the gums of said subject.

8. A method of killing or deactivating any *Candida albicans, E. coli, P. aeruginosa, S. aureus* or methicillin resistant *S. aureus* present on a surface or in a fluid comprising: contacting or applying a compound selected from the group consisting of:

[3,7-(tetra-n-propylamino)-phenothiazin-5-ium]$_P$ X$^{P-}$,
[3,7-(tetra-n-butylamino)-phenothiazin-5-ium]$_P$ X$^{P-}$,
[3,7-(tetra-n-pentylamino)-phenothiazin-5-ium]$_P$ X$^{P-}$,
[3,7-(tetra-iso-pentylamino)-phenothiazin-5-ium]$_P$ X$^{P-}$,
[3-(N,N-di-n-butylamino)-7-(N,N-di-n-propylamino)-phenothiazin-5-ium]$_P$ X$^{P-}$,
[3-(N,N-di-n-hexylamino)-7-(N,N-di-n-propylamino)-phenothiazin-5-ium]$_P$ X$^{P-}$,
[3-(2-ethylpiperidino)-7-(N,N-di-n-pentylamino)-phenothiazin-5-ium]$_P$ X$^{P-}$,
[3-(2-methylpyrrolidino)-7-(N,N-di-n-pentylamino)-phenothiazin-5-ium]$_P$ X$^{P-}$,
[3,7-(N,N-tetra-iso-butylamino)-phenothiazin-5-ium]$_P$ X$^{P-}$,
[3-(N,N-di-n-butylamino)-7-(N,N-di-iso-pentylamino)-phenothiazin-5-ium]$_P$ X$^{P-}$,
[3-(N,N-diethylamino)-7-(N,N-di-n-propylamino)-phenothiazin-5-ium]$_P$ X$^{P-}$,
[3-(N,N-di-n-pentylamino)-7-(N,N-di-n-propylamino)-phenothiazin-5-ium]$_P$ X$^{P-}$,
[3-(N,N-di-n-butylamino)-7-(N,N-di-n-pentylamino)-phenothiazin-5-ium]$_P$ X$^{P-}$, and
[3-((N-ethyl-N-cyclohexyl) amino)-7((-N-ethyl)-N-cyclohexyl) amino-phenothiazin-5-ium]$_P$ X$^{P-}$, wherein X$^{P-}$ is a counteranion and P is 1, 2 or 3,
to said surface or fluid; and
exposing said surface or fluid to which said compound has been applied or contacted to light to activate said compound and thereby kill or deactivate said *Candida albicans, E. coli, P. aeruginosa, S. aureus* or methicillin resistant *S. aureus*.

9. A method for killing or deactivating any *Candida albicans, E. coli, P. aeruginosa, S. aureus* or methicillin resistant *S. aureus* present in a fluid comprising contacting the fluid with a composite formed between:

a compound selected from the group consisting of:
[3,7-(tetra-n-propylamino)-phenothiazin-5-ium]$_P$ X$^{P-}$,
[3,7-(tetra-n-butylamino)-phenothiazin-5-ium]$_P$ X$^{P-}$,
[3,7-(tetra-n-pentylamino)-phenothiazin-5-ium]$_P$ X$^{P-}$,
[3,7-(tetra-iso-pentylamino)-phenothiazin-5-ium]$_P$ X$^{P-}$,
[3-(N,N-di-n-butylamino)-7-(N,N-di-n-propylamino)-phenothiazin-5-ium]$_P$ X$^{P-}$,
[3-(N,N-di-n-hexylamino)-7-(N,N-di-n-propylamino)-phenothiazin-5-ium]$_P$ X$^{P-}$,
[3-(2-ethylpiperidino)-7-(N,N-di-n-pentylamino)-phenothiazin-5-ium]$_P$ X$^{P-}$,
[3-(2-methylpyrrolidino)-7-(N,N-di-n-pentylamino)-phenothiazin-5-ium]$_P$ X$^{P-}$,
[3,7-(N,N-tetra-iso-butylamino)-phenothiazin-5-ium]$_P$ X$^{P-}$,
[3-(N,N-di-n-butylamino)-7-(N,N-di-iso-pentylamino)-phenothiazin-5-ium]$_P$ X$^{P-}$,
[3-(N,N-diethylamino)-7-(N,N-di-n-propylamino)-phenothiazin-5-ium]$_P$ X$^{P-}$,
[3-(N,N-di-n-pentylamino)-7-(N,N-di-n-propylamino)-phenothiazin-5-ium]$_P$ X$^{P-}$,
[3-(N,N-di-n-butylamino)-7-(N,N-di-n-pentylamino)-phenothiazin-5-ium]$_P$ X$^{P-}$, and
[3-((N-ethyl-N-cyclohexyl) amino)-7((-N-ethyl)-N-cyclohexyl) amino-phenothiazin-5-ium]$_P$ X$^{P-}$, wherein X$^{P-}$ is a counteranion and P is 1, 2 or 3,
and a polymer and exposing said fluid to which said composite has been contacted to light to activate said composite and thereby kill or deactivate said *Candida albicans, E. coli, P. aeruginosa, S. aureus* or methicillin resistant *S. aureus*.

10. A method of treating a skin disease selected from the group consisting of psoriasis, acne, vitiligo and eczema comprising administering to a subject in need thereof a therapeutically effective amount of a compound selected from the group consisting of:

[3,7-(tetra-n-propylamino)-phenothiazin-5-ium]$_P$ X$^{P-}$,
[3,7-(tetra-n-butylamino)-phenothiazin-5-ium]$_P$ X$^{P-}$,
[3,7-(tetra-n-pentylamino)-phenothiazin-5-ium]$_P$ X$^{P-}$,
[3,7-(tetra-iso-pentylamino)-phenothiazin-5-ium]$_P$ X$^{P-}$,
[3-(N,N-di-n-butylamino)-7-(N,N-di-n-propylamino)-phenothiazin-5-ium]$_P$ X$^{P-}$,
[3-(N,N-di-n-hexylamino)-7-(N,N-di-n-propylamino)-phenothiazin-5-ium]$_P$ X$^{P-}$,
[3-(2-ethylpiperidino)-7-(N,N-di-n-pentylamino)-phenothiazin-5-ium]$_P$ X$^{P-}$,
[3-(2-methylpyrrolidino)-7-(N,N-di-n-pentylamino)-phenothiazin-5-ium]$_P$ X$^{P-}$,
[3,7-(N,N-tetra-iso-butylamino)-phenothiazin-5-ium]$_P$ X$^{P-}$,
[3-(N,N-di-n-butylamino)-7-(N,N-di-iso-pentylamino)-phenothiazin-5-ium]$_P$ X$^{P-}$,
[3-(N,N-diethylamino)-7-(N,N-di-n-propylamino)-phenothiazin-5-ium]$_P$ X$^{P-}$,
[3-(N,N-di-n-pentylamino)-7-(N,N-di-n-propylamino)-phenothiazin-5-ium]$_P$ X$^{P-}$,
[3-(N,N-di-n-butylamino)-7-(N,N-di-n-pentylamino)-phenothiazin-5-ium]$_P$ X$^{P-}$, and
[3-((N-ethyl-N-cyclohexyl) amino)-7((-N-ethyl)-N-cyclohexyl) amino-phenothiazin-5-ium]$_P$ X$^{P-}$, wherein X$^{P-}$ is a counteranion and P is 1, 2 or 3, and exposing an area of skin of said subject affected by said skin disease to light to render active said compound and thereby effecting said treatment of said skin disease.

11. The method according to any one of claims 1, 8, 9 and 10 wherein the counteranion represented by X$^{P-}$ is selected from the group consisting of F$^-$, Br$^-$, Cl$^-$, I$^-$, NO$_3^-$, SCN$^-$, Cl$_3^-$, ClO$_4^-$, IO$_3^-$, BF$_4^-$, HSO$_4^-$, H$_2$PO$_4^-$, CH$_3$SO$_4^-$, N$_3^-$, SO$_4^{2-}$, HPO$_4^{2-}$, PO$_4^{3-}$, acetate, lactate, citrate, tartrate, glycolate, glycerate, glutamate, β-hydroxyglutamate, glucouronate, gluconate, malate and aspartate.

12. The method according to claim 11 wherein the counteranion represented by X$^{P-}$ is a halide.

13. The method according to any one of claims 1, 8, 9 and 10 wherein said compound [3,7-(tetra-n-butylamino)-phenothiazin-5-ium]$_P$ X$^{P-}$, [3,7-(tetra-n-pentylamino)-phenothiazin-5-ium]$_P$ X$^{P-}$ or [3-((N-ethyl-N-cyclohexyl) amino)-7((-N-ethyl)-N-cyclohexyl) amino-phenothiazin-5-ium]$_P$ X$^{P-}$.

* * * * *